US011692173B2

(12) United States Patent
Kume et al.

(10) Patent No.: US 11,692,173 B2
(45) Date of Patent: Jul. 4, 2023

(54) METHOD FOR INDUCING DIFFERENTIATION OF PLURIPOTENT STEM CELLS INTO HEPATOCYTES

(71) Applicants: TOKYO INSTITUTE OF TECHNOLOGY, Tokyo (JP); KANTO KAGAKU KABUSHIKI KAISHA, Tokyo (JP); CHUGAI SEIYAKU KABUSHIKI KAISHA, Tokyo (JP)

(72) Inventors: Shoen Kume, Tokyo (JP); Nobuaki Shiraki, Tokyo (JP); Hiroyuki Yamaguchi, Isehara (JP); Tomoaki Inoue, Gotemba (JP); Toshito Nakagawa, Gotemba (JP); Jumpei Kiyokawa, Gotemba (JP)

(73) Assignees: TOKYO INSTITUTE OF TECHNOLOGY, Tokyo (JP); KANTO KAGAKU KABUSHIKI KAISHA, Tokyo (JP); CHUGAI SEIYAKU KABUSHIKI KAISHA, Tokyo (JP)

( * ) Notice: Subject to any disclaimer, the term of this patent is extended or adjusted under 35 U.S.C. 154(b) by 532 days.

(21) Appl. No.: 16/755,490

(22) PCT Filed: Oct. 9, 2018

(86) PCT No.: PCT/JP2018/037531

§ 371 (c)(1),
(2) Date: Apr. 10, 2020

(87) PCT Pub. No.: WO2019/073951

PCT Pub. Date: Apr. 18, 2019

(65) Prior Publication Data

US 2021/0207085 A1 Jul. 8, 2021

(30) Foreign Application Priority Data

Oct. 12, 2017 (JP) ................................ 2017-198201

(51) Int. Cl.
*C12N 5/071* (2010.01)

(52) U.S. Cl.
CPC ........ *C12N 5/067* (2013.01); *C12N 2501/119* (2013.01); *C12N 2501/12* (2013.01);
(Continued)

(58) Field of Classification Search
None
See application file for complete search history.

(56) References Cited

U.S. PATENT DOCUMENTS

2018/0120298 A1 5/2018 Takezawa

FOREIGN PATENT DOCUMENTS

EP 2 457 998 A1 6/2012
JP 2011-41552 A 3/2011
(Continued)

OTHER PUBLICATIONS

Vinken, Mathieu; Rogiers, Vera; Protocols in In Vitro Hepatocyte Research, Humana Press, New York, 2015 (Year: 2015).*
(Continued)

*Primary Examiner* — David W Berke-Schlessel
(74) *Attorney, Agent, or Firm* — Birch, Stewart, Kolasch & Birch, LLP

(57) ABSTRACT

The present invention provides, in order to prepare matured hepatocytes analogous in various points to primary hepatocytes, a method for preparing hepatocytes or cells that can be differentiated into hepatocytes from pluripotent stem cells, comprising the steps of: (1) culturing the pluripotent stem cells in a medium containing an activator of an activin receptor-like kinase-4,7; (2) culturing the cells obtained in the step (1) in a medium containing a bone morphogenetic factor and a fibroblast growth factor; (3) culturing the cells obtained in the step (2) in a medium containing an activator of a hepatocyte growth factor receptor and an activator of an
(Continued)

oncostatin M receptor; and (4) culturing the cells obtained in the step (3) to obtain hepatocytes or cells that can be differentiated into hepatocytes, wherein in at least one of the steps (2), (3) and (4), cells are cultured on a high-density collagen gel membrane.

6 Claims, 8 Drawing Sheets

(52) U.S. Cl.
CPC .... *C12N 2501/155* (2013.01); *C12N 2501/16* (2013.01); *C12N 2501/237* (2013.01); *C12N 2501/727* (2013.01); *C12N 2533/54* (2013.01); *C12Y 207/11* (2013.01)

(56) References Cited

FOREIGN PATENT DOCUMENTS

| | | | |
|---|---|---|---|
| WO | WO 2011/130402 | A2 | 10/2011 |
| WO | WO 2014/124527 | A1 | 8/2014 |
| WO | WO 2016/158417 | A1 | 10/2016 |

OTHER PUBLICATIONS

Aleahmad et al., "Heparin/Collagen 3D Scaffold Accelerates Hepatocyte Differentiation of Wharton's Jelly-Derived Mesenchymal Stem Cells", Tissue Engineering and Regenerative Medicine, vol. 14, No. 4, 2017, pp. 443-452.

Baharvand et al., "Differentiation of human embryonic stem cells into hepatocytes in 2D and 3D culture systems in vitro", International Journal of Developmental Biology, vol. 50, 2006, pp. 645-652.

Nakai et al.,"Collagen vitrigel promotes hepatocytic differentiation of induced pluripotent stem cells into functional hepatocyte-like cells", Biology Open, vol. 8, 2019, pp. 1-14.

Oshikata-Miyazaki et al., "Development of an oxygenation culture method for activating the liver-specific functions of HepG2 cells utilizing a collagen vitrigel membrane chamber", Cytotechnology, vol. 68, 2016, pp. 1801-1811.

Razban et al., "Engineered Heparan Sulfate-Collagen IV Surfaces Improve Human Mesenchymal Stem Cells Differentiation to Functional Hepatocyte-Like Cells", Journal of Biomaterials and Tissue Engineering, vol. 4, 2014, pp. 811-822.

Supplementary European Search Report for European Patent Application No. 18866218.3, dated May 3, 2021.

Wang et al., "Hepatocytic differentiation of rhesus monkey embryonic stem cells promoted by collagen gels and growth factors", Cell Biology International, vol. 35, No. 8, Apr. 21, 2011, pp. 775-781.

International Preliminary Report on Patentability, dated Apr. 14, 2020, and English translation of the Written Opinion of the International Searching Authority, dated Jan. 8, 2019, (Forms PCT/IB/373 and PCT/ISA/237) for International Application No. PCT/JP2018/037531.

Asplund et al., "One Standardized Differentiation Procedure Robustly Generates Homogenous Hepatocyte Cultures Displaying Metabolic Diversity from a Large Panel of Human Pluripotent Stem Ceils", Stem Cell Reviews and Reports, 2016, vol. 12, pp. 90-104.

Hannan et al., "Production of hepatocyte-like cells from human pluripotent stem cells", Nature protocols, 2013, vol. 8, No. 2, pp. 430-437.

International Search Report for PCT/JP2018/037531 dated Jan. 8, 2019.

Miyamoto et al., "Direct Cryopreservation of Primary Hepatocytes and ES Cells using a Collagen Vitrigel Membrane", Cryobiology and Cryotechnology, 2010, vol. 56, No. 1, pp. 47-50.

Ogawa et al., "Three-dimensional culture and cAMP signaling promote the maturation of human pluripotent stem cell-derived hepatocytes", Development, 2013, vol. 140, pp. 3285-3296.

Takezawa, "Development of a Novel Material "Collagen Vitrigel Membrane" Functioned as a Cellular Scaffold and Its Concept for the Practical Applications in Medical and Pharmaceutical Fields", Journal of Pharmaceutical Science and Technology, Japan, 2015, vol. 75, No. 6, pp. 344-353.

Written Opinion of the International Searching Authority for PCT/JP2018/037531 (PCT/ISA/237) dated Jan. 8, 2019.

* cited by examiner

| | Day 15 | Day 20 | Day 25 |
|---|---|---|---|
| AFP positive | 69.6 | 36.1 | 6.2 |
| ALB positive | 0.3 | 23.7 | 54.3 |
| AFP / ALB double positive | 28.3 | 39.7 | 32.6 |

Scale bar = 100 µm

Figure 7

| No. | Symbol | GenBank Acc. | Gene size | Position | Exon_junction | Description | Gene size | Position | Oligo dT | Random 6 mers | Exon_junction | Variants | Variants check |
|---|---|---|---|---|---|---|---|---|---|---|---|---|---|
| 1 | NANOG | NM_024865.2 | 2098 | 375 | 1/3 | Homo sapiens Nanog homeobox (NANOG), mRNA. | 2098 | 375 | NG | OK | 1/3 | | 1/1 |
| 2 | POU5F1 | NM_002701.4 | 1411 | 506 | 2/4 | Homo sapiens POU class 5 homeobox 1 (POU5F1), transcript variant 1, mRNA. | 1411 | 506 | OK | OK | 2/4 | | 1/3 |
| 3 | SOX2 | NM_003106.3 | 2520 | 1081 | 0/0 | Homo sapiens SRY (sex determining region Y)-box 2 (SOX2), mRNA. | 2520 | 1081 | OK | OK | 0/0 | | 1/1 |
| 4 | CD9 | NM_001769 | 1321 | 298 | 1/7 | Homo sapiens CD9 molecule (CD9), mRNA. | 1321 | 298 | OK | OK | 1/7 | | 1/1 |
| 5 | DNMT3B | NM_175848 | 4263 | 1257 | 1/21 | Homo sapiens DNA (cytosine-5-)-methyltransferase 3 beta (DNMT3B), transcript variant 2, mRNA. | 4263 | 1257 | NG | OK | 1/21 | NM_006892,NM_175849,NM_175850,N | 6/6 |
| 6 | GABRB3 | NM_000814 | 5763 | 677 | 1/8 | Homo sapiens gamma-aminobutyric acid (GABA) A receptor, beta 3 (GABRB3), transcript variant 1, mRNA. | 5763 | 677 | NG | OK | 1/8 | NM_021912,NM_001191320,NM_00119 | 4/4 |
| 7 | GAL | NM_015973 | 778 | 359 | 1/5 | Homo sapiens galanin prepropeptide (GAL), mRNA. | 778 | 359 | OK | OK | 1/5 | | 1/1 |
| 8 | GDF3 | NM_020634 | 1224 | 337 | 1/1 | Homo sapiens growth differentiation factor 3 (GDF3), mRNA. | 1224 | 337 | OK | OK | 1/1 | | 1/1 |
| 9 | GRB7 | NM_005310 | 2285 | 1110 | 1/14 | Homo sapiens growth factor receptor-bound protein 7 (GRB7), transcript variant 1, mRNA. | 2285 | 1110 | OK | OK | 1/14 | NM_001030002,NM_001242442,NM_00 | 3/3 |
| 10 | IFITM1 | NM_003641 | 733 | 423 | 1/1 | Homo sapiens interferon induced transmembrane protein 1 (9-27) (IFITM1), mRNA. | 733 | 423 | OK | OK | 1/1 | | 1/1 |
| 11 | PODXL | NM_005397 | 5911 | 1389 | 1/7 | Homo sapiens podocalyxin-like (PODXL), transcript variant 2, mRNA. | 5911 | 1389 | NG | OK | 1/7 | NM_001018111 | 2/2 |
| 12 | TDGF1 | NM_001174136 | 1794 | 428 | 1/5 | Homo sapiens teratocarcinoma-derived growth factor 1 (TDGF1), transcript variant 2, mRNA. | 1794 | 428 | OK | OK | 1/5 | NM_003212 | 2/2 |
| 13 | ZFP42 | NM_174900 | 2646 | 308 | 1/3 | Homo sapiens zinc finger protein 42 homolog (mouse) (ZFP42), mRNA. | 2646 | 308 | NG | OK | 1/3 | | 1/1 |
| 14 | SOX7 | NM_031439.2 | 3219 | 260 | 1/1 | Homo sapiens SRY (sex determining region Y)-box 7 (SOX7), mRNA. | 3219 | 260 | NG | OK | 1/1 | | 1/1 |
| 15 | LAMB1 | NM_002291.2 | 5868 | 4733 | 1/33 | Homo sapiens laminin, beta 1 (LAMB1), mRNA. | 5868 | 4733 | OK | OK | 1/33 | | 1/1 |
| 16 | HNF1B | NM_000458.2 | 2842 | 1767 | 1/8 | Homo sapiens HNF1 homeobox B (HNF1B), transcript variant 1, mRNA. | 2842 | 1767 | OK | OK | 1/8 | NM_001165923 | 3/3 |
| 17 | GSC | NM_173849.2 | 1217 | 800 | 1/2 | Homo sapiens goosecoid homeobox (GSC), mRNA. | 1217 | 800 | OK | OK | 1/2 | | 1/1 |
| 18 | NODAL | NM_018055.4 | 2086 | 846 | 1/2 | Homo sapiens nodal homolog (mouse) (NODAL), mRNA. | 2086 | 846 | OK | OK | 1/2 | | 1/1 |
| 19 | FOXA2 | NM_021784.4 | 2429 | 286 | 1/1 | Homo sapiens forkhead box A2 (FOXA2), transcript variant 1, mRNA. | 2429 | 286 | NG | OK | 1/1 | NM_153675 | 2/2 |
| 20 | SOX17 | NM_022454.3 | 2390 | 1549 | 2/1 | Homo sapiens SRY (sex determining region Y)-box 17 (SOX17), mRNA. | 2390 | 1549 | OK | OK | 2/1 | | 1/1 |
| 21 | CXCR4 | NM_001008540 | 1912 | 982 | 2/2 | Homo sapiens chemokine (C-X-C motif) receptor 4 (CXCR4), transcript variant 1, mRNA. | 1912 | 982 | OK | OK | 2/2 | NM_003467 | 2/2 |
| 22 | GATA4 | NM_002052.3 | 3419 | 1542 | 1/6 | Homo sapiens GATA binding protein 4 (GATA4), mRNA. | 3419 | 1542 | NG | OK | 1/6 | | 1/1 |
| 23 | GATA6 | NM_005257.4 | 3770 | 1890 | 1/6 | Homo sapiens GATA binding protein 6 (GATA6), mRNA. | 3770 | 1890 | NG | OK | 1/6 | | 1/1 |
| 24 | AFP | NM_001134.1 | 2032 | 332 | 1/14 | Homo sapiens alpha-fetoprotein (AFP), mRNA. | 2032 | 332 | NG | OK | 1/14 | | 1/1 |
| 25 | CYP3A7 | NM_000765 | 2085 | 587 | 2/12 | Homo sapiens cytochrome P450, family 3, subfamily A, polypeptide 7 | 2085 | 587 | OK | OK | 2/12 | | 1/1 |
| 26 | DLK1 | NM_003836.5 | 1588 | 316 | 2/4 | Homo sapiens delta-like 1 homolog (Drosophila) (DLK1), mRNA. | 1588 | 316 | OK | OK | 2/4 | | 1/2 |
| 27 | PROX1 | NM_002763.3 | 3098 | 2265 | 1/4 | Homo sapiens prospero homeobox 1 (PROX1), mRNA. | 3098 | 2265 | OK | OK | 1/4 | | 1/1 |
| 28 | TBX3 | NM_005996.3 | 4754 | 1587 | 1/6 | Homo sapiens T-box 3 (TBX3), transcript variant 1, mRNA. | 4754 | 1587 | NG | OK | 1/6 | NM_016569 | 2/2 |
| 29 | SERPINA1 | NM_000295.4 | 3220 | 1850 | 0/4 | Homo sapiens serpin peptidase inhibitor, clade A (alpha-1 antiproteinase, antitrypsin), member 1 (SERPINA1), transcript variant 1. | 3220 | 1850 | OK | OK | 0/4 | NM_001002235,NM_001002236,NM_00 | 11/11 |
| 30 | AHSG | NM_001622.2 | 1584 | 289 | 1/6 | Homo sapiens alpha-2-HS-glycoprotein (AHSG), mRNA. | 1584 | 289 | OK | OK | 1/6 | | 1/1 |
| 31 | ALB | NM_000477.5 | 2264 | 310 | 1/14 | Homo sapiens albumin (ALB), mRNA. | 2264 | 310 | NG | OK | 1/14 | | 1/1 |
| 32 | APOA4 | NM_000482.3 | 1480 | 258 | 1/2 | Homo sapiens apolipoprotein A-IV (APOA4), mRNA. | 1480 | 258 | OK | OK | 1/2 | | 1/1 |
| 33 | ASGR1 | NM_001671.4 | 1519 | 384 | 1/8 | Homo sapiens asialoglycoprotein receptor 1 (ASGR1), transcript variant 1, mRNA. | 1519 | 384 | OK | OK | 1/8 | NM_001197216 | 2/2 |
| 34 | KRT8 | NM_001256282 | 1807 | 73 | 1/8 | Homo sapiens keratin 8 (KRT8), transcript variant 1, mRNA. | 1807 | 73 | NG | OK | 1/8 | | 1/4 |
| 35 | KRT18 | NM_000224.2 | 1485 | 1299 | 1/6 | Homo sapiens keratin 18 (KRT18), transcript variant 1, mRNA. | 1485 | 1299 | OK | OK | 1/6 | NM_199187 | 2/2 |
| 36 | FABP1 | NM_001443.2 | 598 | 441 | 1/3 | Homo sapiens fatty acid binding protein 1, liver (FABP1), mRNA. | 598 | 441 | OK | OK | 1/3 | | 1/1 |
| 37 | FGG | NM_000509.4 | 1685 | 1275 | 1/9 | Homo sapiens fibrinogen gamma chain (FGG), transcript variant gamma-A, mRNA. | 1685 | 1275 | OK | OK | 1/9 | NM_021870 | 2/2 |
| 38 | G6PC | NM_000151.3 | 3096 | 328 | 1/4 | Homo sapiens glucose-6-phosphatase, catalytic subunit (G6PC), mRNA. | 3096 | 328 | NG | OK | 1/4 | | 1/1 |
| 39 | PCK2 | NM_004563.2 | 2221 | 413 | 1/9 | Homo sapiens phosphoenolpyruvate carboxykinase 2 (mitochondrial) (PCK2), nuclear gene encoding mitochondrial protein, transcript variant 1, mRNA. | 2221 | 413 | NG | OK | 1/9 | NM_001018073 | 2/2 |
| 40 | RBP4 | NM_006744.3 | 941 | 442 | 1/5 | Homo sapiens retinol binding protein 4, plasma (RBP4), mRNA. | 941 | 442 | OK | OK | 1/5 | | 1/1 |
| 41 | TAT | NM_000353.2 | 2757 | 1381 | 1/11 | Homo sapiens tyrosine aminotransferase (TAT), nuclear gene encoding mitochondrial protein, mRNA. | 2757 | 1381 | OK | OK | 1/11 | | 1/1 |
| 42 | TF | NM_001063.3 | 2368 | 2028 | 1/16 | Homo sapiens transferrin (TF), mRNA. | 2368 | 2028 | OK | OK | 1/16 | | 1/1 |
| 43 | TDO2 | NM_005651.3 | 1702 | 494 | 1/11 | Homo sapiens tryptophan 2,3-dioxygenase (TDO2), mRNA. | 1702 | 494 | OK | OK | 1/11 | | 1/1 |
| 44 | HHEX | NM_002729.4 | 1772 | 675 | 1/3 | Homo sapiens hematopoietically expressed homeobox (HHEX), mRNA. | 1772 | 675 | OK | OK | 1/3 | | 1/1 |
| 45 | HNF1A | NM_000545.5 | 3241 | 2317 | 2/9 | Homo sapiens HNF1 homeobox A (HNF1A), mRNA. | 3241 | 2317 | OK | OK | 2/9 | | 1/1 |
| 46 | HNF4A | NM_178849.2 | 4707 | 905 | 1/9 | Homo sapiens hepatocyte nuclear factor 4, alpha (HNF4A), transcript variant 1, mRNA. | 4707 | 905 | NG | OK | 1/9 | NM_001030003,NM_001030004,NM_17 | 7/7 |
| 47 | AHR | NM_001621.4 | 6247 | 1479 | 1/10 | Homo sapiens aryl hydrocarbon receptor (AHR), mRNA. | 6247 | 1479 | NG | OK | 1/10 | | 1/1 |
| 48 | NR1I3 | NM_001077473 | 1120 | 807 | 1/7 | Homo sapiens nuclear receptor subfamily 1, group I, member 3 (NR1I3), transcript variant 12, mRNA. | 1120 | 807 | OK | OK | 1/7 | NM_001077480,NM_001077481,NM_00 | 15/15 |
| 49 | NR1I2 | NM_003889.3 | 4446 | 2880 | 1/8 | Homo sapiens nuclear receptor subfamily 1, group I, member 2 (NR1I2), transcript variant 1, mRNA. | 4446 | 2880 | NG | OK | 1/8 | NM_033013,NM_022002 | 3/3 |
| 50 | NR1H3 | NM_005693.3 | 1839 | 1290 | 1/9 | Homo sapiens nuclear receptor subfamily 1, group H, member 3 (NR1H3), transcript variant 1, mRNA. | 1839 | 1290 | OK | OK | 1/9 | NM_001130101,NM_001130102,NM_00 | 5/5 |

Figure 8

| | | | | | | | | | | | | | |
|---|---|---|---|---|---|---|---|---|---|---|---|---|---|
| 51 | NR1H4 | NM_001206979 | 2325 | 1412 | 1/10 | Homo sapiens nuclear receptor subfamily 1, group H, member 4 (NR1H4), transcript variant 1, mRNA. | 2325 | 1412 | OK | OK | 1/10 | NM_001206977,NM_001206978,NM_00 | 6/6 |
| 52 | RXRA | NM_002957.4 | 5547 | 180 | 1/9 | Homo sapiens retinoid X receptor, alpha (RXRA), mRNA. | 5547 | 180 | NG | OK | 1/9 | | 1/1 |
| 53 | NR3C1 | NM_001204258 | 6801 | 2026 | 1/8 | Homo sapiens nuclear receptor subfamily 3, group C, member 1 (glucocorticoid receptor) (NR3C1), transcript variant 1, mRNA. | 6801 | 2026 | NG | OK | 1/8 | NM_001024094,NM_001204258,NM_00 | 15/15 |
| 54 | PPARA | NM_001001928 | 9865 | 552 | 1/7 | Homo sapiens peroxisome proliferator-activated receptor alpha (PPARA), transcript variant 3, mRNA. | 9865 | 552 | NG | OK | 1/7 | NM_005036 | 2/5 |
| 55 | CYP1A1 | NM_000499 | 2608 | 1971 | 0/6 | Homo sapiens cytochrome P450, family 1, subfamily A, polypeptide 1 | 2608 | 1971 | OK | OK | 0/6 | | 1/1 |
| 56 | CYP1A2 | NM_000761 | 3127 | 989 | 0/6 | Homo sapiens cytochrome P450, family 1, subfamily A, polypeptide 2 | 3127 | 989 | NG | OK | 0/6 | | 1/1 |
| 57 | CYP2A6 | NM_000762 | 1775 | 1212 | 1/8 | Homo sapiens cytochrome P450, family 2, subfamily A, polypeptide 6 (CYP2A6), mRNA | 1775 | 1212 | OK | OK | 1/8 | | 1/1 |
| 58 | CYP2C8 | NM_000770 | 1924 | 1389 | 1/8 | Homo sapiens cytochrome P450, family 2, subfamily C, polypeptide 8, transcript variant 1 | 1924 | 1389 | OK | OK | 1/8 | NM_001198853,NM_001198854,NM_00 | 4/5 |
| 59 | CYP2E1 | NM_000773 | 1867 | 1026 | 1/8 | Homo sapiens cytochrome P450, family 2, subfamily E, polypeptide 1 | 1867 | 1026 | OK | OK | 1/8 | | 1/1 |
| 60 | CYP2D6 | NM_000106 | 1673 | 1419 | 1/8 | Homo sapiens cytochrome P450, family 2, subfamily D, polypeptide 6 , | 1673 | 1419 | OK | OK | 1/8 | NM_001025161 | 2/2 |
| 61 | CYP3A4 | NM_017460 | 2792 | 1595 | 1/12 | Homo sapiens cytochrome P450, family 3, subfamily A, polypeptide 4 | 2792 | 1595 | OK | OK | 1/12 | NM_001202855 | 2/4 |
| 62 | CYP7A1 | NM_000780 | 2875 | 235 | 1/5 | Homo sapiens cytochrome P450, family 7, subfamily A, polypeptide 1 | 2875 | 235 | NG | OK | 1/5 | | 1/1 |
| 63 | ABCB4 | NM_000443.3 | 3967 | 2627 | 1/27 | Homo sapiens ATP-binding cassette, sub-family B (MDR/TAP), member 4 (ABCB4), transcript variant A, mRNA. | 3967 | 2627 | OK | OK | 1/27 | NM_018850,NM_018849 | 3/3 |
| 64 | ABCC1 | NM_004996.3 | 6564 | 1681 | 1/30 | Homo sapiens ATP-binding cassette, sub-family C (CFTR/MRP), member 1 (ABCC1), mRNA. | 6564 | 1681 | NG | OK | 1/30 | | 1/7 |
| 65 | ABCC3 | NM_003786.3 | 5153 | 1530 | 1/30 | Homo sapiens ATP-binding cassette, sub-family C (CFTR/MRP), member 3 (ABCC3), transcript variant 1, mRNA. | 5153 | 1530 | NG | OK | 1/30 | NM_001144070 | 2/4 |
| 66 | ABCG2 | NM_004827.2 | 4445 | 1394 | 2/15 | Homo sapiens ATP-binding cassette, sub-family G (WHITE), member 2 (ABCG2), transcript variant 1, mRNA. | 4445 | 1394 | NG | OK | 2/15 | NM_001257386 | 2/2 |
| 67 | SLC10A1 | NM_003049.3 | 1631 | 594 | 1/4 | Homo sapiens solute carrier family 10 (sodium/bile acid cotransporter family), member 1 (SLC10A1), mRNA. | 1631 | 594 | OK | OK | 1/4 | | 1/1 |
| 68 | SLC22A1 | NM_003057.2 | 1921 | 790 | 1/10 | Homo sapiens solute carrier family 22 (organic cation transporter), member 1 (SLC22A1), transcript variant 1, mRNA. | 1921 | 790 | OK | OK | 1/10 | NM_153187 | 2/2 |
| 69 | SLC22A2 | NM_003058.3 | 2512 | 1464 | 1/10 | Homo sapiens solute carrier family 22 (organic cation transporter), member 2 (SLC22A2), mRNA. | 2512 | 1464 | OK | OK | 1/10 | | 1/2 |
| 70 | SLCO1B1 | NM_006446.4 | 2800 | 1577 | 1/14 | Homo sapiens solute carrier organic anion transporter family, member 1B1 (SLCO1B1), mRNA. | 2800 | 1577 | OK | OK | 1/14 | | 1/1 |
| 71 | SLCO1B3 | NM_019844.3 | 3014 | 2007 | 1/15 | Homo sapiens solute carrier organic anion transporter family, member 1B3 (SLCO1B3), mRNA. | 3014 | 2007 | OK | OK | 1/15 | | 1/1 |
| 72 | SLCO2B1 | NM_007256.4 | 4382 | 3036 | 0/13 | Homo sapiens solute carrier organic anion transporter family, member 2B1 (SLCO2B1), transcript variant 1, mRNA. | 4382 | 3036 | OK | OK | 0/13 | NM_001145211,NM_001145212 | 3/3 |
| 73 | UGT1A1 | NM_000463.2 | 2357 | 430 | 0/4 | Homo sapiens UDP glucuronosyltransferase 1 family, polypeptide A1 (UGT1A1), mRNA. | 2357 | 430 | NG | OK | 0/4 | | 1/1 |
| 74 | GSTA2 | NM_000846.4 | 1326 | 432 | 1/6 | Homo sapiens glutathione S-transferase alpha 2 (GSTA2), mRNA. | 1326 | 432 | OK | OK | 1/6 | | 1/1 |
| 75 | ATP5G1 | NM_005175.2 | 863 | 455 | 1/4 | Homo sapiens ATP synthase, H+ transporting, mitochondrial Fo complex, subunit C1 (subunit 9) (ATP5G1), nuclear gene encoding mitochondrial protein, transcript variant 1, mRNA. | 863 | 455 | OK | OK | 1/4 | NM_001002027 | 2/2 |
| 76 | POLG | NM_002693.2 | 4464 | 3732 | 1/22 | Homo sapiens polymerase (DNA directed), gamma (POLG), transcript variant 1, mRNA. | 4464 | 3732 | OK | OK | 1/22 | NM_001126131 | 2/2 |
| 77 | PPARGC1A | NM_013261.3 | 6318 | 521 | 1/12 | peroxisome proliferator-activated receptor gamma, coactivator 1 alpha (PPARGC1A) | 6318 | 521 | NG | OK | 1/12 | | 1/1 |
| 78 | UCP2 | NM_003355.2 | 1646 | 1209 | 1/7 | Homo sapiens uncoupling protein 2 (mitochondrial, proton carrier) (UCP2), nuclear gene encoding mitochondrial protein, mRNA. | 1646 | 1209 | OK | OK | 1/7 | | 1/1 |
| 79 | ARG1 | NM_001244438 | 1499 | 683 | 1/7 | Homo sapiens arginase, liver (ARG1), transcript variant 1, mRNA. | 1499 | 683 | OK | OK | 1/7 | NM_000045 | 2/2 |
| 80 | ASL | NM_001024943 | 2061 | 1296 | 1/15 | Homo sapiens argininosuccinate lyase (ASL), transcript variant 1, mRNA. | 2061 | 1296 | OK | OK | 1/15 | NM_000048,NM_001024944,NM_00102 | 4/4 |
| 81 | ASS1 | NM_000050.4 | 1863 | 1358 | 1/15 | Homo sapiens argininosuccinate synthase 1 (ASS1), transcript variant 1, mRNA. | 1863 | 1356 | OK | OK | 1/15 | NM_054012 | 2/2 |
| 82 | CPS1 | NM_001122633 | 5738 | 4340 | 1/38 | Homo sapiens carbamoyl-phosphate synthase 1, mitochondrial (CPS1), nuclear gene encoding mitochondrial protein, transcript | 5738 | 4340 | OK | OK | 1/38 | NM_001875,NM_001122634 | 3/3 |
| 83 | NAGS | NM_153006.2 | 2086 | 1459 | 1/6 | Homo sapiens N-acetylglutamate synthase (NAGS), mRNA. | 2086 | 1459 | OK | OK | 1/6 | | 1/1 |
| 84 | OTC | NM_000531.5 | 1647 | 87 | 0/9 | Homo sapiens ornithine carbamoyltransferase (OTC), nuclear gene encoding mitochondrial protein, mRNA. | 1647 | 87 | NG | OK | 0/9 | | 1/1 |
| 85 | KRT19 | NM_002276.4 | 1490 | 840 | 1/5 | Homo sapiens keratin 19 (KRT19), mRNA. | 1490 | 840 | OK | OK | 1/5 | | 1/1 |
| 86 | KRT7 | NM_005556.3 | 1753 | 1008 | 1/8 | Homo sapiens keratin 7 (KRT7), mRNA. | 1753 | 1008 | OK | OK | 1/8 | | 1/1 |
| 87 | AQP1 | NM_198098.2 | 2807 | 775 | 1/3 | Homo sapiens aquaporin 1 (Colton blood group) (AQP1), transcript variant 1, mRNA. | 2807 | 775 | NG | OK | 1/3 | NM_001185060,NM_001185061,NM_00 | 4/5 |
| 88 | HES1 | NM_005524.3 | 1475 | 918 | 1/3 | Homo sapiens hairy and enhancer of split 1, (Drosophila) (HES1), mRNA. | 1475 | 918 | OK | OK | 1/3 | | 1/1 |
| 89 | GUSB | NM_000181 | 2321 | 1773 | 1/11 | Homo sapiens glucuronidase, beta (GUSB), mRNA. | 2321 | 1773 | OK | OK | 1/11 | | 1/1 |
| 90 | HPRT1 | NM_000194 | 1435 | 684 | 2/8 | Homo sapiens hypoxanthine phosphoribosyltransferase 1 (HPRT1), mRNA. | 1435 | 684 | OK | OK | 2/8 | | 1/1 |
| 91 | PGK1 | NM_000291 | 2439 | 1086 | 1/10 | Homo sapiens phosphoglycerate kinase 1 (PGK1), mRNA. | 2439 | 1086 | OK | OK | 1/10 | | 1/1 |
| 92 | ACTB | NM_001101.3 | 1852 | 1135 | 1/5 | Homo sapiens actin, beta (ACTB), mRNA. | 1852 | 1135 | OK | OK | 1/5 | | 1/1 |
| 93 | GAPDH | NM_002046.4 | 1401 | 415 | 1/8 | Homo sapiens glyceraldehyde-3-phosphate dehydrogenase (GAPDH), transcript variant 1, mRNA. | 1401 | 415 | OK | OK | 1/8 | NM_001256799 | 2/2 |
| 94 | TBP | NM_003194 | 1921 | 954 | 1/7 | Homo sapiens TATA box binding protein (TBP), mRNA. | 1921 | 954 | OK | OK | 1/7 | NM_001172085 | 2/2 |
| 95 | B2M | NM_004048 | 987 | 122 | 1/3 | Homo sapiens beta-2-microglobulin (B2M), mRNA. | 987 | 122 | OK | OK | 1/3 | | 1/1 |
| 96 | PPIA | NM_021130 | 2276 | 522 | 1/4 | Homo sapiens peptidylprolyl isomerase A (cyclophilin A) (PPIA), mRNA. | 2276 | 522 | NG | OK | 1/4 | | 1/3 |

METHOD FOR INDUCING DIFFERENTIATION OF PLURIPOTENT STEM CELLS INTO HEPATOCYTES

TECHNICAL FIELD

The present invention relates to a method for preparing hepatocytes or cells that can be differentiated into hepatocytes, hepatocytes or cells that can be differentiated into hepatocytes and a method for evaluating property of a test substance by using the hepatocytes.

BACKGROUND ART

Drugs are mostly metabolized in the liver and changed in medicinal effect or become toxic. Because of this, it is necessary to check toxicity of drug candidate substances to the liver in developing drugs. Currently, hepatotoxicity is evaluated by in vivo tests using experimental animals such as mice and in vitro tests using human primary hepatocytes. However, the tests using experimental animals are unfavorable because it is difficult to accurately evaluate toxicity to human hepatocytes because of "boundary of species difference" and also in view of animal protection. On the other hand, human primary hepatocytes have problems in limited supply and large lot-difference, and in that the activity of drug-metabolizing enzymes decreases in a short time from initiation of culture.

Pluripotent stem cells such as ES cells and iPS cells have differentiation potential into any types of somatic cells including hepatocytes. If human-derived pluripotent stem cells can be differentiated into mature hepatocytes and hepatotoxicity tests can be carried out by using the mature hepatocytes, the aforementioned problems can be overcome. For the reason, it has been strongly desired to develop a technique for inducing differentiation of human pluripotent stem cells into mature hepatocytes.

Techniques for inducing differentiation of human pluripotent stem cells into mature hepatocytes have been previously reported in some literatures; for example, the present inventors reported a method for differentiating into hepatocytes using nanofiber as a scaffolding (Non Patent Literature 1).

CITATION LIST

Non Patent Literature

Non Patent Literature 1: Yamazoe et al., 2013, J. Cell Sci. 126, 5391-9

SUMMARY OF INVENTION

Technical Problem

The hepatocytes obtained by the method described in Non Patent Literature 1 expressed differentiation markers such as ALB and SERPINA1 at a high level; however, the expression levels of transporters and metabolic enzymes were not sufficient.

In the circumstances, it is an object of the present invention to provide a means for preparing mature hepatocytes, which are analogous in various points to primary hepatocytes.

Solution to Problem

The present inventors conducted intensive studies with a view to attaining the above object. As a result, they found that hepatocytes having a high degree of maturation can be obtained by culturing endoderm cells derived from iPS cells on Collagen Vitrigel (registered trademark) membrane.

Collagen Vitrigel is used for culturing various types of cells and sometimes for hepatocyte-related cells. For example, it is reported that HepG2 cells derived from human liver cancer were cultured by using Collagen Vitrigel (Oshikata-Miyazaki and Takezawa, 2016, Cytotechnology 68, 1801-1811). However, there are no reports that cells during the differentiation process, such as endoderm cells, are cultured; and that highly matured hepatocytes were obtained by such culturing.

The present invention was achieved based on the above findings.

More specifically, the present invention provides the following [1] to [9].

[1] A method for preparing hepatocytes or cells that can be differentiated into hepatocytes from pluripotent stem cells, comprising the following steps (1) to (4):

(1) culturing the pluripotent stem cells in a medium containing an activator of an activin receptor-like kinase-4,7;

(2) culturing the cells obtained in the step (1) in a medium containing a bone morphogenetic factor and a fibroblast growth factor;

(3) culturing the cells obtained in the step (2) in a medium containing an activator of a hepatocyte growth factor receptor and an activator of an oncostatin M receptor; and (4) culturing the cells obtained in the step (3) to obtain hepatocytes or cells that can be differentiated into hepatocytes, wherein in at least one of the steps (2), (3) and (4), the cells are cultured on a high-density collagen gel membrane.

[2] The method according to [1], wherein in all of the steps (2), (3) and (4), the cells are cultured on the high-density collagen gel membrane.

[3] The method according to [1] or [2], wherein the activator of an activin receptor-like kinase-4,7 is activin A; the bone morphogenetic factor is BMP4; the fibroblast growth factor is FGF10; the activator of a hepatocyte growth factor receptor is HGF; and the activator of an oncostatin M receptor is oncostatin M.

[4] Hepatocytes or cells that can be differentiated into hepatocytes, prepared by a method comprising the following steps (1) to (4):

(1) culturing the pluripotent stem cells in a medium containing an activator of an activin receptor-like kinase-4,7;

(2) culturing the cells obtained in the step (1) in a medium containing a bone morphogenetic factor and a fibroblast growth factor;

(3) culturing the cells obtained in the step (2) in a medium containing an activator of a hepatocyte growth factor receptor and an activator of an oncostatin M receptor; and (4) culturing the cells obtained in the step (3) to obtain hepatocytes or cells that can be differentiated into hepatocytes, wherein in at least one of the steps (2), (3) and (4), the cells are cultured on a high-density collagen gel membrane.

[5] The hepatocytes or cells that can be differentiated into hepatocytes according to [4], wherein in all of the steps (2), (3) and (4), the cells are cultured on the high-density collagen gel membrane.

[6] The hepatocytes or cells that can be differentiated into hepatocytes according to [4] or [5], wherein the activator of an activin receptor-like kinase-4,7 is activin A; the bone morphogenetic factor is BMP4; the fibroblast growth factor is FGF10, the activator of a hepatocyte growth factor receptor is HGF and the activator of an oncostatin M receptor is oncostatin M.

[7] Hepatocytes prepared from pluripotent stem cells, wherein an expression level of CYP3A4 is 2% or more of an expression level of CYP3A4 in primary hepatocytes.

[8] A method for evaluating the property of a test substance, comprising the following steps:

(1) culturing the hepatocytes according to any one of [4] to [6] in a medium containing the test substance to allow the hepatocytes into contact with the test substance; and (2) measuring an indicator related to the property to evaluate the property of the test substance.

[9] The method according to [8], wherein the property is safety and the indicator related to the property is a survival rate of the hepatocytes.

The specification encompasses the contents described in the specification and/or drawings of Japanese Patent Application No. 2017-198201, on which the priority of the present application is based.

Advantageous Effects of Invention

The present invention provides hepatocytes having a high degree of maturation and a method for producing the hepatocytes. The hepatocytes having a high degree of maturation are useful for evaluating safety of drugs or the like.

Figure 1:
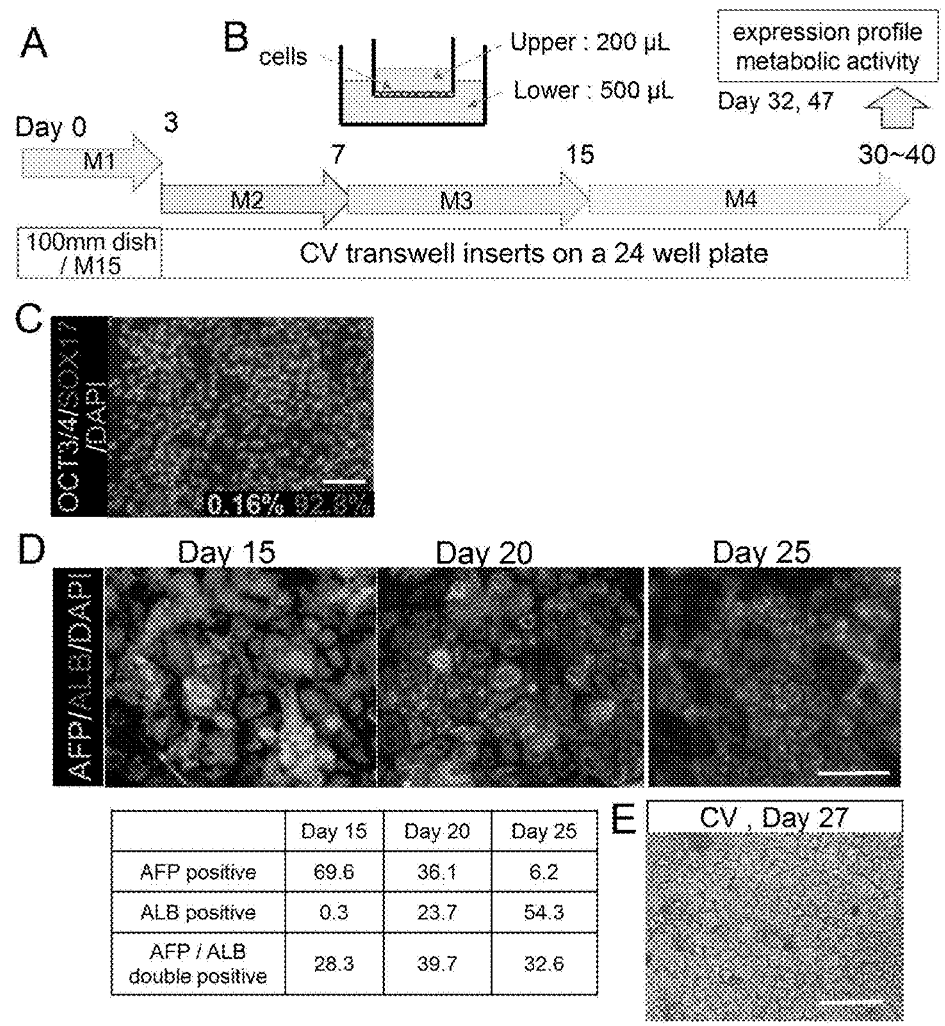
FIG. 1 Differentiation of human iPS cells into the hepatocyte line on Collagen Vitrigel membrane.

(A) Schematic diagram of the differentiation of human iPSCs into hepatocytes. Undifferentiated human iPSCs were differentiated into the endoderm on M15 cells. Human iPS cell-derived endoderm cells on day 3 were dissociated and frozen until use. For use in differentiation, the frozen endoderm was thawed and seeded onto Collagen Vitrigel (CV) membrane transwell insert (B). A medium (200 μL) was supplied into the upper chamber of the transwell insert; whereas the medium (500 μL) was supplied into the lower chamber thereof. The mediums used in individual differentiation stages are shown. Human iPS cell-derived hepatocytes on day 30 (D30) to day 47 (D47) after initiation of differentiation were subjected to expression profile analysis or metabolic activity tests. Scale bar: 100 μm. (C) Immunochemical analysis of human iPS cell-derived endoderm cells. Green: OCT3/4 (0.16±0.02%); Red: SOX17 (92.8±0.14%). (D) Immunochemical analysis of differentiated human iPSCs on day 15, day 20 and day 25 with nuclear counterstaining (DAPI, blue), α-fetoprotein (AFP, green) and albumin (ALB, red). Percentages of cells AFP single positive cells, ALB-single positive cells and AFP/ALB-double positive cells are shown in the table. (E) In typical phase contrast image of human iPS cell-derived hepatocytes differentiated on CV membrane on day 27, polygonal cells analogous to morphology of hepatocytes were shown. Scale bar: 100 μm.

Figure 2:
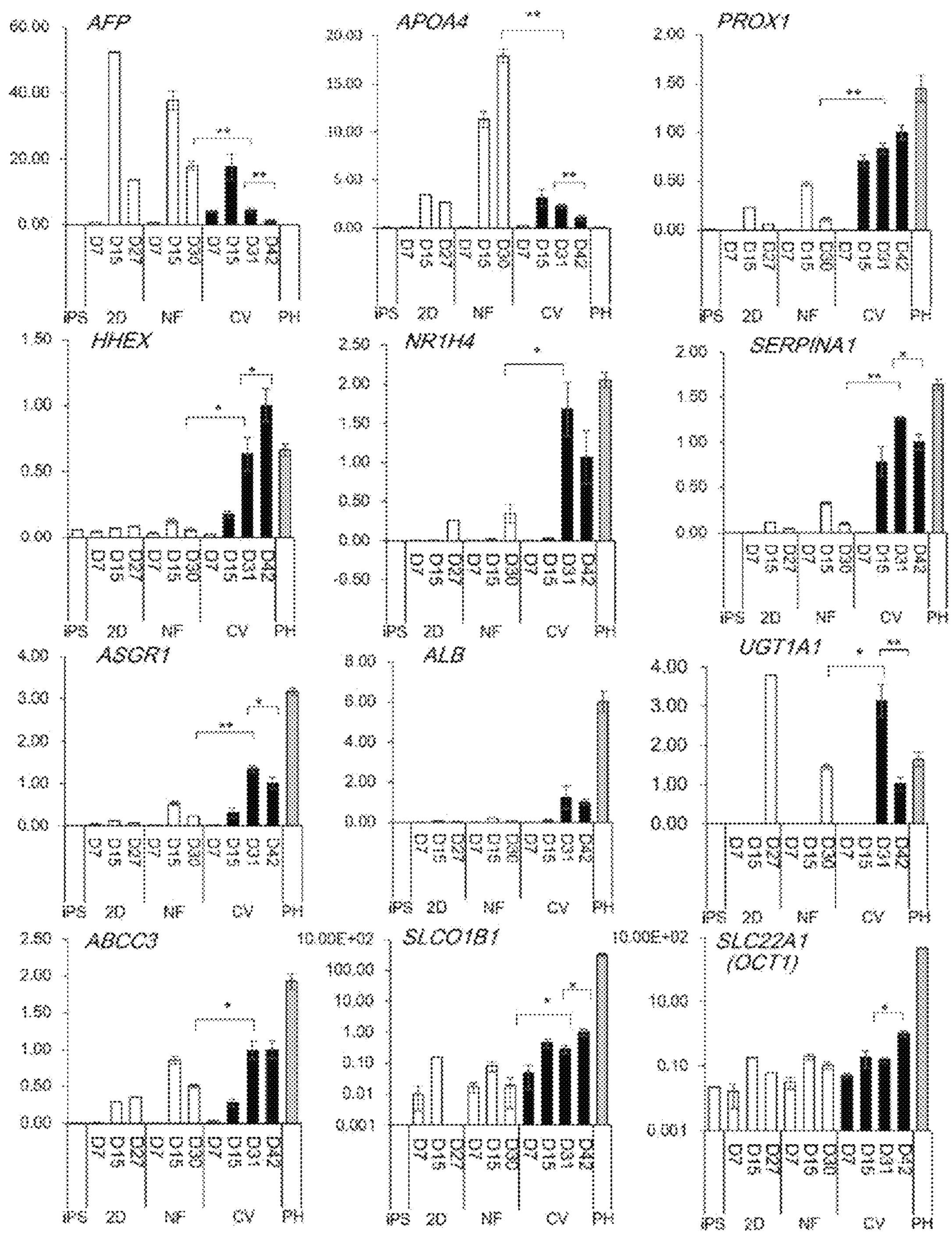

FIG. 2 Expressions of hepatic markers in differentiated human iPSCs on Collagen Vitrigel membrane, nanofiber matrix or ordinary cell-culture plate coated with Synthemax (registered trademark) II.

Graphs shows expression levels of various gene transcripts (quantified by real time PCR) of undifferentiated human iPS cells (iPS) or differentiated human iPS cells, which were differentiated on an ordinary cell-culture plate (2D), nanofiber (NF) or Collagen Vitrigel (CV) membrane for 7 days, 15 days, 27 days, 30 days or 42 days. Primary hepatocytes (PH) were used as a reference. For differentiated human iPS cells, values represent means±S.D (n=3). The values are relative values based on the value of human iPS cells differentiated on CV for 42 days (regarded as 1). A significant difference was observed between a culture on CV for 31 days and a culture on NF for 30 days; or between a culture on CV for 31 days and a culture on CV for 40 days. by Student t-test (Significance level: *$p<0.05$ or **$p<0.01$).

Figure 3:
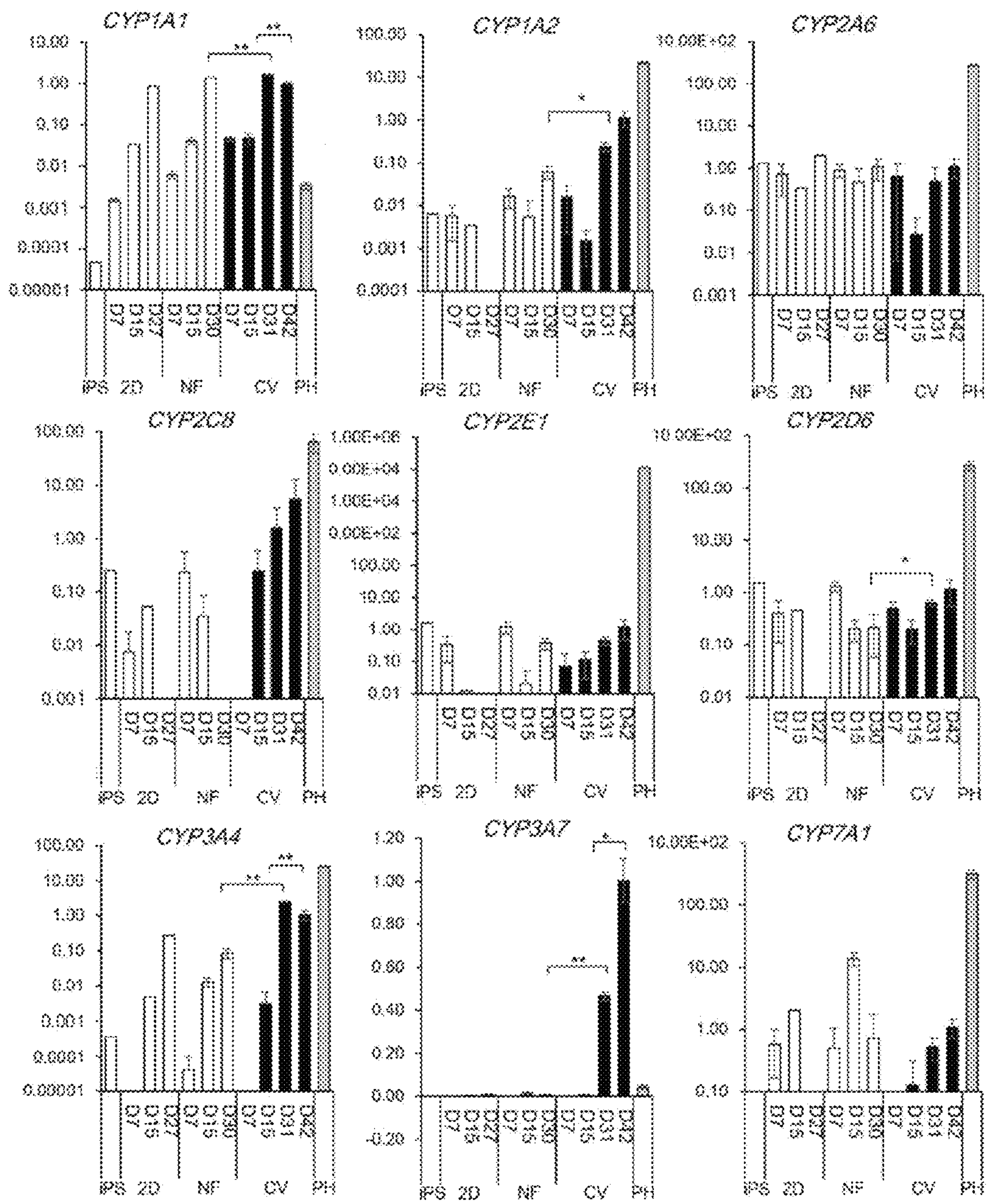

FIG. 3 Expressions of CYP metabolizing enzyme genes in human iPS cells differentiated on Vitrigel, nanofiber or ordinary cell-culture plate.

Graphs show expression levels of various metabolizing enzymes (which were quantified by real time PCR) in undifferentiated human iPS cells or iPS cell-derived hepatocytes cultured on an ordinary cell-culture plate (2D), nanofiber (NF) or CV membrane. Primary hepatocytes (PH) were used as a reference. For differentiated human iPS cells, the values represent means±S.D (n=3). The values are relative values based on the value of human iPS cells differentiated on CV for 42 days (regarded as 1). A significant difference was observed between a culture on CV for 31 days and a culture on NF for 30 days; or between a culture on CV for 31 days and a culture on CV for 40 days by Student t-test (Significance level: *$p<0.05$ or **$p<0.01$).

Figure 4:
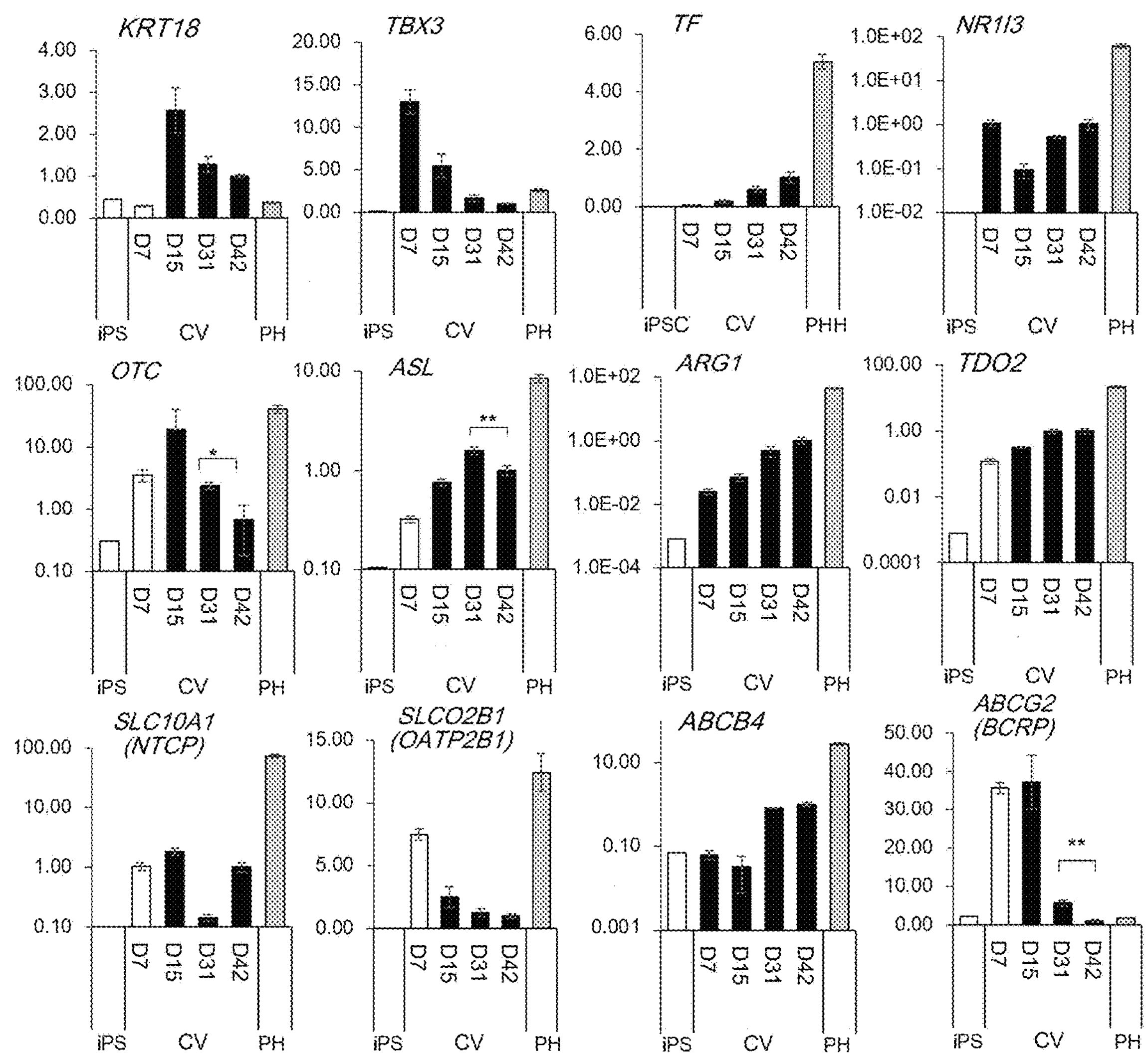

FIG. 4 Hepatic gene expression in undifferentiated human iPS cells or differentiated human iPS cells on CV membrane.

Expression levels of various genes associated with hepatic differentiation or maturation (function) of the hepatocytes were quantified by real time PCR in undifferentiated iPS cells or iPS cell-derived hepatocytes cultured on CV membrane. Primary hepatocytes (PH) were used as a reference. The values represent means±S.D (n=3). The values are relative values based on the value of human iPS cells differentiated on CV for 42 days (regarded as 1). A significant difference was observed between a culture on CV for 31 days and a culture on CV for 40 days, by Student t-test (Significance level: *$p<0.05$ or **$p<0.01$)

Figure 5:
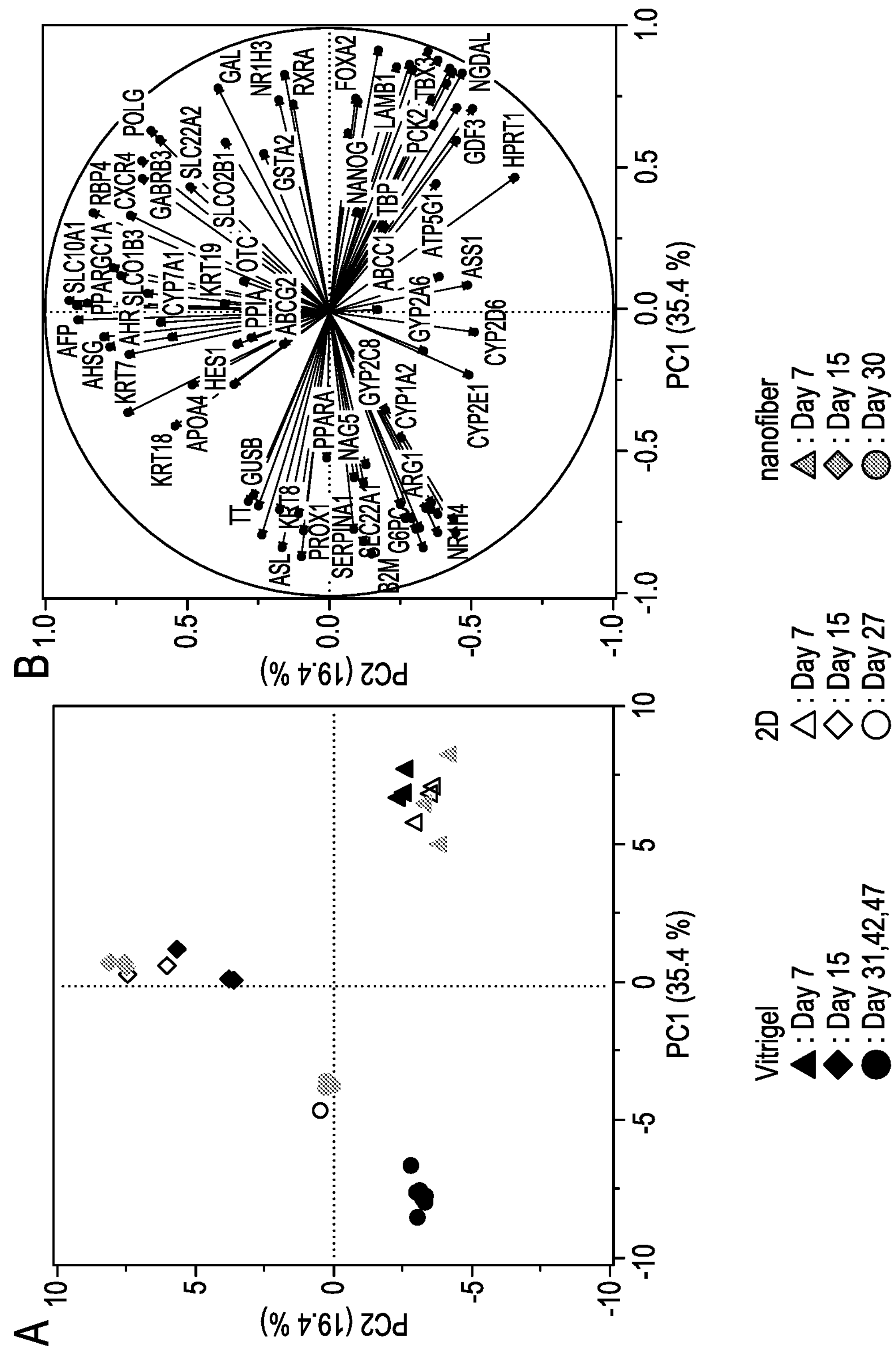

FIG. 5 Principal component analysis (PCA) of gene expression, which shows that the late human iPS cell-derived hepatocytes cultured on CV are different from those cultured on NF or in an ordinary 2D environment.

In PCA, it was confirmed that the hepatic gene expression profile shown by human iPS cell-derived hepatocytes cultured on Vitrigel in the late stage tends to differ from that shown by the hepatocytes cultured on an ordinary cell-culture plate or a nanofiber substrate.

(A) PCA of Gene Expression Profile.

Expression data of 96 genes from PrimerArray were analyzed. Each sample was mapped to two dimensional plot along with its expression levels of genes of significance for PC1 and PC2 axes, to give the largest variance. Data obtained from human iPS cell-derived differentiated cells cultured on CV membrane (black), ordinary cell-culture plate (white) or nanofiber (grey) were shown by triangles at day 7, diamonds at day 15 and circles at day 27 to 47 after initiation of differentiation.

(B) Individual Genes are Plotted According to their Values of PC1 and PC2 Axes.

Figure 6:
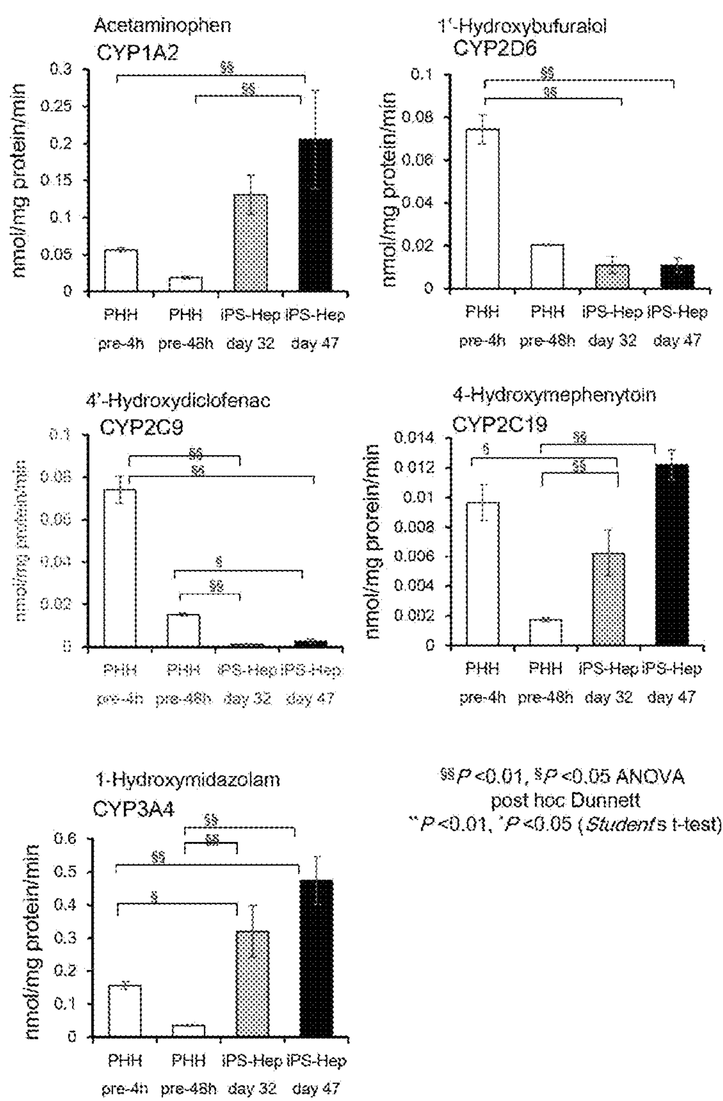

FIG. 6 CYP activities in human iPS cell-derived hepatocytes on day 32 and day 47 after initiation of differentiation.

CYP1A2, CYP2C9, CYP2C19, CYP2D6 and CYP3A4 activities in cultures of hepatocytes derived from human iPS cells on day 32 (grey bars) or day 47 (black bars) after initiation of differentiation were determined by LC/MS. As the values, the values obtained at 2 hours were normalized to the protein content per well per min and shown. Cryopreserved primary hepatocytes (open bars) pre-cultured for 4 h (pre-4 h) or 48 h (pre-48 h) are used as references. The values represent means±S.D (n=3). Significance of differences are shown as § P<0.05 or §§ P<0.01. A group of data obtained in primary hepatocytes (pre-4 h) or primary hepatocytes (pre-48 h) and a group of data obtained in human iPS cell-derived hepatocytes were compared by one-way ANOVA using the post-hoc Dunnett's test.

FIG. 7 The figure shows list of primers used in PrimerArray (Well ID 1 to 50).

FIG. 8 The figure shows list of primers used in PrimerArray (Well ID 51 to 96).

DESCRIPTION OF EMBODIMENTS

The present invention will be more specifically described below.

(A) Method for Preparing Hepatocytes or Cells that can be Differentiated into Hepatocytes The method for preparing hepatocytes or cells that can be differentiated into hepatocytes of the present invention is a method for preparing hepatocytes or cells that can be differentiated into hepatocytes from pluripotent stem cells, comprising: (1) culturing the pluripotent stem cells in a medium containing an activator of an activin receptor-like kinase-4,7; (2) culturing the cells obtained in the step (1) in a medium containing a bone morphogenetic factor and a fibroblast growth factor; (3) culturing the cells obtained in the step (2) in a medium containing an activator of a hepatocyte growth factor receptor and an activator of an oncostatin M receptor; and (4) culturing the cells obtained in the step (3) to obtain hepatocytes or cells that can be differentiated into hepatocytes, wherein in at least one of the steps (2), (3) and (4), the cells are cultured on a high-density collagen gel membrane.

The "pluripotent stem cells" refer to the cells which have a self-replication ability, can be cultured in vitro and have pluripotency to differentiate into cells that constitute an individual body. Examples thereof include embryonic stem cells (ES cells), pluripotent stem cells (GS cells) derived from fetal primordial germ cells, artificial pluripotent stem cells (iPS cells) derived from somatic cells and somatic stem cells. The pluripotent stem cells preferably used in the present invention are iPS cells or ES cells and particularly preferably human iPS cells and human ES cells.

ES cells may not be particularly limited in type and acquisition method as long as they are ES cells derived from a mammal. Examples of the mammal include, but are not limited to mouse, rat, guinea pig, hamster, rabbit, cat, dog, sheep, cow, horse, goat, monkey and human. The mammal is preferably a mouse or a human and further preferably a human.

ES cells can be established generally by repeating an operation consisting of culturing a blastocyst stage fertilized egg together with feeder cells, separating proliferated cells derived from inner cell mass from each other and culturing them to finally obtain a cell line.

The iPS cells (induced pluripotent stem cells) refer to the cells that acquired pluripotency, more specifically, the cells that acquired the same pluripotency as ES cells by introducing genes encoding several types of transcription factors (pluripotent factors, by which the somatic cells acquire pluripotency) into the somatic cells (for example, fibroblasts). As the "pluripotency factor", various factors have been reported. Examples thereof include, but are not particularly limited to, Oct family (for example, Oct3/4), Sox family (for example, Sox2, Sox1, Sox3, Sox15, Sox17), Klf family (for example, Klf4, Klf2), Myc family (for example, c-Myc, N-Myc, L-Myc), Nanog and LIN28. A method for establishing iPS cells has been reported in many literatures and can refer to them (for example, Takahashi et al., Cell, 2006, 126:663-676; Okita et al., Nature, 2007, 448: 313-317: Wernig et al., Nature, 2007, 448: 318-324; Maherali et al., Cell Stem Cell, 2007, 1: 55-70; Park et al., Nature, 2007, 451: 141-146; Nakagawa et al., Nat Biotechnol 2008, 26: 101-106; Wernig et al., Cell Stem Cell, 2008, 10: 10-12; Yu et al., Science, 2007, 318: 1917-1920; Takahashi et al., Cell, 2007, 131: 861-872; Stadtfeld et al., Science, 2008, 322: 945-949).

Pluripotent stem cells can be cultured and maintained by a method usually used in the art. ES cells derived from a mammal can be cultured by a routine method and can be maintained by using feeder cells such as mouse fetal fibroblasts (MEF cells) in a medium, such as DMEM medium, containing leukemia inhibitory factor, KSR (knockout serum replacement), fetal bovine serum (FBS), non-essential amino acid(s), L-glutamine, pyruvate, penicillin, streptomycin and/or β-mercaptoethanol. Also, iPS cells can be cultured by a routine method and can be maintained by using feeder cells such as MEF cells in a medium, such as DMEM/F12 medium, containing, bFGF, KSR (knockout serum replacement), non-essential amino acid(s), L-glutamine, penicillin, streptomycin and/or β-mercaptoethanol.

The "cells that can be differentiated into hepatocytes" are not limited as long as the cells can be differentiated into hepatocytes. Examples thereof include liver progenitor cells and hepatoblasts. The terms "liver progenitor cells" and "hepatoblasts" are general terms that can be easily understood by those skilled in the art. The "liver progenitor cells" can be defined, for example, as cells positive to α-fetoprotein and negative to albumin; whereas the "hepatoblasts" can be defined as cells positive to both α-fetoprotein and albumin.

The "high-density collagen gel" refers to collagen gel constituted of high-density collagen fibers like in the connective tissue of a living body and having excellent strength and transparency. As the high-density collagen gel, Collagen Vitrigel (registered trademark by the National Agriculture and Food Research Organization) can be mentioned (Toshiaki Takezawa: Journal of the Society of Biotechnology. 91: 214-217, 2013, WO2012/026531, Japanese Patent Laid-Open No. 2012-115262). The high-density collagen gel can be prepared by gelatinizing, for example, collagen sol and drying the gelatinized collagen like glass, followed by rehydrating. The density of collagen fibers in high-density collagen gel is preferably 21 to 45% (W/V), more preferably 26 to 40% (W/V) and further preferably 31 to 35% (W/V).

Culture on a high-density collagen gel membrane can be carried out in any manner. A high-density collagen gel membrane is provided on the bottom part of a tubular frame body and cells are preferably cultured on the bottom part.

The method for preparing hepatocytes or cells that can be differentiated into hepatocytes of the present invention comprises the following steps (1) to (4).

In the step (1), pluripotent stem cells are cultured in a medium containing an activator of an activin receptor-like kinase-4,7. Through culturing, the pluripotent stem cells are differentiated into endoderm cells. Differentiation of the pluripotent stem cells into endoderm cells is confirmed by evaluating changes in proteins and genes (endoderm markers) expressed in an endoderm cell-specific manner. Change in expression of endoderm markers can be evaluated in accordance with, for example, a method for evaluating expression of a protein by an antigen-antibody reaction and/or a method for evaluating gene expression by quantitative RT-PCR. Examples of the endoderm markers include SOX17 and FOXA2.

The activator of activin receptor-like kinase (ALK)-4,7 is selected from substances having an action to activate ALK-4 and/or ALK-7. Examples of the activator of an activin receptor-like kinase-4,7 that can be used herein include activin, Nodal and Myostatin. Preferably activin is used. As the activin, activin A, B, C, D and AB are known. Any one of the activins can be used. As the activin to be used, particularly preferably activin A is mentioned. Also, as the activin to be used, activin derived from a mammal such as a human and a mouse can be used; however, activin derived from the same animal species as that of the stem cells for use in differentiation is preferably used; for example, when human-derived pluripotent stem cells are used as the starting cells, human-derived activin, particularly human-derived activin A, is preferably used. These activins are commercially available.

As the medium to be used in the step (1), a basal medium supplemented with an activator of an activin receptor-like kinase-4,7, can be used. As the medium, M1 medium described in Examples can be mentioned. The concentration of an activator of an activin receptor-like kinase-4,7 in the medium is appropriately set in accordance with the type of the activin. When human activin A is used, the concentration of the activator is usually 3 to 500 ng/mL and preferably, 5 to 200 ng/mL.

Examples of the basal medium include BME medium, BGjB medium, CMRL 1066 medium, Glasgow MEM medium, Improved MEM medium, IMDM medium, Medium 199 medium, Eagles MEM medium, αMEM medium, DMEM medium, Ham's medium, RPMI 1640 medium, Fischer's medium, William's E medium and a mixed medium of these. However, the medium is not particularly limited as long as it can be used for culturing animal cells. These mediums are commercially available.

The medium to be used in the step (1) may contain a serum replacement. Examples of the serum replacement include albumin, transferrin, a fatty acid, a collagen precursor, trace elements (for example, zinc, selenium), B-27 supplement, E5 supplement, E6 supplement, N2 supplement, knockout serum replacement (KSR), 2-mercaptoethanol, 3'-thiolglycerol and an equivalent of any one of these. These serum replacements are commercially available. Preferably, xeno-free B-27 supplement or xeno-free knockout serum replacement (KSR) can be mentioned and may be added in the medium in a concentration of, for example, 0.01 to 10 wt % and preferably 0.1 to 2.0 wt %. Also, the medium to be used in the step (1) may contain other additives such as a lipid, an amino acid (for example, non-essential amino acid), a vitamin, a growth factor, a cytokine, an antioxidant, 2-mercaptoethanol, pyruvate, a buffer, an inorganic salt, an antibiotics substance (for example, penicillin and streptomycin) and an antibacterial agent (for example, amphotericin B).

The culture of the step (1) is preferably carried out on M15 feeder cells. Owing to the feeder cells, pluripotent stem cells can be efficiently induced into the endoderm cells (Shiraki et al., 2008, Stem Cells 26, 874-85). The culture in this step does not need to be carried out on a high-density collagen gel membrane.

The culture of the step (1) is carried out at a temperature suitable for culturing cells (usually 30 to 40° C. preferably approximately 37° C.) and usually carried out in a $CO_2$ incubator. The culture period is usually 1 to 5 days and preferably 3 to 4 days.

In the step (2), the cells obtained in the step (1) are cultured in a medium containing a bone morphogenetic factor and a fibroblast growth factor.

Examples of the bone morphogenetic factor (BMP) include BMP2, BMP3, BMP4, BMP5, BMP6 and BMP7. Preferably, BMP2, BMP4 and further preferably BMP4 is used. These may be a naturally occurring protein or a recombinant protein.

Examples of the fibroblast growth factor (FGF) include FGF1, FGF2 (bFGF), FGF3, FGF4, FGF5, FGF6, FGF7, FGF8, FGF9, FGF10, FGF11, FGF12, FGF13, FGF14, FGF15, FGF16, FGF17, FGF18, FGF19, FGF20, FGF21, FGF22 and FGF23. Preferably, FGF2 (bFGF), FGF5, FGF7 and FGF10; and further preferably FGF10 is used. These may be a naturally occurring protein or a recombinant protein.

As the medium to be used in the step (2), a basal medium supplemented with a bone morphogenetic factor and a fibroblast growth factor, can be used. As such a medium, M2 medium described in Examples can be mentioned. The concentration of a bone morphogenetic factor in the medium is appropriately set in accordance with the type of bone morphogenetic factor. When BMP4 is used, the concentration of the bone morphogenetic factor is usually 2 to 200 ng/mL and preferably 5 to 50 ng/mL. The concentration of a fibroblast growth factor is appropriately set in accordance with the type of fibroblast growth factor. When FGF10 is used, the concentration of the fibroblast growth factor is usually 2 to 100 ng/mL and preferably 5 to 50 ng/mL. As the basal medium, the same medium as used in the step (1) can be used. The medium in step (2) may contain a serum replacement and other additives similarly to the medium used in the step (1).

The culture of the step (2) is preferably carried out on a high-density collagen gel membrane.

The culture of the step (2) is carried out at a temperature suitable for culturing cells (usually 30 to 40° C. preferably approximately 37° C.) and usually carried out in a $CO_2$ incubator. The culture period is usually 2 to 6 days and preferably 2 to 4 days.

In the step (3), the cells obtained in the step (2) are cultured in a medium containing an activator of a hepatocyte growth factor receptor and an activator of an oncostatin M receptor.

As an example of the activator of the hepatocytes growth factor (HGF) receptor (Met), HGF can be mentioned.

As an example of the activator of an oncostatin M receptor, oncostatin M can be mentioned.

As the medium to be used in the step (3), a basal medium supplemented with an activator of a hepatocyte growth factor receptor and an activator of an oncostatin M receptor, can be used. As such a medium, M3 medium described in Examples can be mentioned. The concentration of an activator of a hepatocyte growth factor receptor in the medium is appropriately set in accordance with the type of the activator. When HGF is used, the concentration of the activator is usually 10 to 250 ng/mL and preferably 10 to 150 ng/mL. The concentration of an activator of an oncostatin M receptor in the medium is appropriately set in accordance with the type of the activator. When oncostatin M is used, the concentration of the activator is usually, 5 to 200 ng/mL and preferably 10 to 60 ng/mL. As the basal medium, the same medium as the medium used in the step (1) can be used. The medium in step (3) may contain a serum replacement and other additives similarly to the medium used in the step (1).

The culture of the step (3) is preferably carried out on a high-density collagen gel membrane.

The culture of the step (3) is carried out at a temperature suitable for culturing cells (usually 30 to 40° C., preferably approximately 37° C.) and usually carried out in a $CO_2$ incubator. The culture period is usually 4 to 12 days and preferably 4 to 10 days.

In the step (4), the cells obtained in the step (3) are cultured to obtain hepatocytes or cells that can be differentiated into hepatocytes.

As the medium of step (4), a medium containing Cellartis (registered trademark) Hepatocyte Maintenance Medium can be used. As such a medium, M4 medium described in Examples, can be mentioned.

The culture of the step (4) is preferably carried out on a high-density collagen gel membrane.

The culture of the step (4) is carried out at a temperature suitable for culturing cells (usually 30 to 40° C., preferably approximately 37° C.) and usually carried out in a $CO_2$ incubator. The culture period is usually 7 days or more and preferably 7 to 40 days.

As mentioned above, culture on a high-density collagen gel membrane may be carried out in at least one of the steps (2), (3) and (4), preferably, in all of steps (2), (3) and (4) (that is, a step from the endoderm cells to hepatocytes or a step from endoderm cells to cells that can be differentiated into hepatocytes). However, only in the step (3) and (4) or only in the step (4), culture may be carried out on a high-density collagen gel membrane.

(B) Hepatocytes or Cells that can be Differentiated into Hepatocytes

Hepatocytes or cells that can be differentiated into hepatocytes according to the present invention are characterized by being prepared by a method comprising the following steps (1) to (4):

(1) culturing the pluripotent stem cells in a medium containing an activator of an activin receptor-like kinase-4, 7;

(2) culturing the cells obtained in the step (1) in a medium containing a bone morphogenetic factor and a fibroblast growth factor;

(3) culturing the cells obtained in the step (2) in a medium containing an activator of a hepatocyte growth factor receptor and an activator of an oncostatin M receptor; and (4) culturing the cells obtained in the step (3) to obtain hepatocytes or cells that can be differentiated into hepatocytes, wherein in at least one of the steps (2), (3) and (4), the cells are cultured on a high-density collagen gel membrane.

The hepatocytes of the present invention are novel hepatocytes having a high degree of maturation that has never been found in hepatocytes derived from pluripotent stem cells known in the art (for example, hepatocytes derived from pluripotent stem cells described in Yamazoe et al., 2013, J. Cell Sci. 126, 5391-9).

Note that, as described above, in the specification, "products" such as "hepatocytes" and "cells that can be differentiated into hepatocytes" are defined not by a structure and characteristics but by a production method. This is because cells are part of a living body, and thus, the structure and characteristics are extremely complicated and work for identifying the cells requires extremely expensive cost and time.

The hepatocytes of the present invention include hepatocytes prepared from pluripotent stem cells and characterized in that the expression level of CYP3A4 is 2% or more of that of the primary hepatocytes.

The primary hepatocytes to be used as a comparative subject are not particularly limited, commercially available hepatocytes, for example, cells manufactured by Bioreclamation IVT and used in Examples, can be used. Note that, if the preculture period of primary hepatocytes becomes long, the expression level of CYP3A4 decreases. For the reason, primary hepatocytes not precultured are used.

The expression level of CYP3A4 can be measured by a method known in the art, for example, RT-PCR.

The expression level of CYP3A4 is preferably 2% or more of that of the primary hepatocytes, preferably, 3% or more, more preferably 4% or more and further preferably 5% or more.

(C) Evaluation Method

A method for evaluating the property of a test substance of the present invention is characterized by comprising: culturing the hepatocytes in a medium containing the test substance to contact the hepatocytes with the test substance; and measuring an indicator related to the property to evaluate the property of the test substance.

As the property as an evaluation target, safety of a test substance (more specifically, hepatotoxicity) can be mentioned. In this case, as a subject to be measured, i.e., an indicator, a survival rate of hepatocytes can be mentioned. The survival rate of hepatocytes can be determined in accordance with a method known in the art, more specifically, the following (a) to (g):

(a) a method for measuring, e.g., LDH, AST and ALT;

(b) a method of staining hepatocytes with, e.g., Trypan Blue to count stained cells (dead cells);

(c) a method of measuring respiratory activity of cells; more specifically, a method of using a substance, such as MTT and WST, generating color depending on the respiratory activity to measure respiratory activity based on the color;

(d) a method of measuring ATP, i.e., an energy source that cells have; more specifically, a method of lysing cells and measuring the level of ATP contained in the cell lysate;

(e) a method of measuring mitochondrial toxicity;

(f) a method of measuring oxidative stress; and (g) a method of measuring a biological matter (e.g., Caspase) involved in apoptosis (cells death).

The property serving as an evaluation target is not limited to safety, for example, a medicinal effect of a test substance and a pharmacokinetic can be used as an evaluation target.

If the medicinal effect of a test substance is evaluated, a subject to be measured, i.e., indicator can be appropriately selected depending on the disease to which the medicinal effect is to be produced. For example, if the medicinal effect on diabetes is evaluated, metabolism of sugar in hepatocytes may be measured.

If a pharmacokinetic of a test substance is employed as an evaluation target, e.g., activity of a drug metabolizing enzyme and transporter function can be used as a subject to be measured.

In the evaluation method of the present invention, e.g., cholestasis and fatty liver induction can be used as an evaluation target.

Examples

The present invention will be more specifically described by way of the following Examples; however, the present invention is not limited to these.

(A) Materials and Methods (1) Human iPS Cell Line

Undifferentiated human iPS cell line, ChiPS18 cells (Asplund et al., 2015, Stem Cell Rev. Reports) were maintained in AK02 StemFit medium (Ajinomoto) on cell culture dishes (Invitrogen) pre-coated with Synthemax II (registered trademark). For methionine deprivation, ChiPS18 cells were cultured in StemFit medium (Ajinomoto) complete medium or Met-deficiency KA01 medium (Ajinomoto).

(2) Preparation of Collagen Vitrigel Membrane Chamber

A collagen xerogel membrane is manufactured by Kanto Chemical Co., Inc. (Tokyo, Japan). Briefly, Collagen Vitrigel membrane was prepared by the following three steps as previously reported (Oshikata-Miyazaki and Takezawa, 2016 Cytotechnology 68, 1801-1811; Yamaguchi et al., 2013, Toxicol. Sci. 135, 347-355; Yamaguchi et al., 2016, J. Appl. Toxicol. 36, 1025-1037): 1) a gelation step in which an opaque soft gel was formed from 0.2 ml of 0.25% type I collagen sol, in a culture plate of 35 mm in diameter; 2) a vitrification step in which the gel was dried into a hard material; and 3) a rehydration step in which the vitrified material was converted into a thin transparent gel membrane enhanced in gel strength by supplying water. Subsequently, the Collagen Vitrigel membrane was vitrified again on a separable sheet to prepare a collagen xerogel membrane defined as a dried Collagen Vitrigel membrane containing no free water. The collagen xerogel membrane was pasted onto the bottom end of a plastic cylinder having an inner-outer diameter of 11-13 mm and a length of 15 mm and two hangers were connected to the upper end of the cylinder. In this manner, a collagen xerogel membrane chamber that can be easily converted into a Collagen Vitrigel membrane chamber by rehydration with a culture medium was prepared, as previously reported (Oshikata-Miyazaki and Takezawa, 2016, Cytotechnology 68, 1801-1811; Yamaguchi et al., 2013, Toxicol. Sci. 135, 347-355; Yamaguchi et al., 2016, J. Appl. Toxicol. 36, 1025-1037).

(3) Differentiation of iPS Cells into Hepatic Lineage

Undifferentiated ChiPS18 cells were first differentiated into the endoderm by using M15 cells. Briefly, plates of 100 mm in diameter were pre-coated with frozen M15 feeder cells treated with mitomycin at a density of $5\times10^6$ cells/plate. In order to differentiate into the endoderm, undifferentiated ChiPS18 cells were seeded onto M15 cell-coated plates of 100 mm in diameter at a density of $5\times10^5$ cells/plate and cultured in an endoderm differentiation medium, i.e., M1 medium, supplemented with 3 μM CHIR99021, for one day. Subsequently, the medium was replaced with M1 (not containing CHIR99021) and the cells were cultured for another two days. M1 medium consists of DMEM, 4,500 mg/L glucose, NEAA, L-Gln, penicillin, streptomycin, 0.1 mM I-ME serum-free B27 supplement 100 ng/mL recombinant human activin A. On day 3 (D3), ChiPS18-derived endoderm cells were collected and frozen at a concentration of $2.0\times10^6$ cells/ml in Bambanker hRM (NIPPON Genetics Co., Ltd., CS-07-001) and stored in liquid $N_2$ until use.

For hepatic differentiation, the frozen endoderm cells were thawed and seeded onto rehydrated Vitrigel (CV) membrane 24-well inserts (ad-MED Vitrigel™ 2, KANTO KAGAKU, culture area: 0.33 $cm^2$/insert) at a concentration of $1\times10^5$ cells/well. The volume of the medium in the upper layer of the transwell was 200 μL; whereas the volume of the medium in the lower layer thereof was 500 μL. The medium used for differentiation was: M2 medium for D3-D7 and M3 medium for D7-D15 and M4 medium for D15 to 30 or day 15 to 40. M2 medium consists of Knockout DMEM/F12 supplemented with NEAA, L-Gln, PS, 0.1 mM β-ME, serum free B27 supplement, 10 ng/ml recombinant human FGF10 and 10 ng/ml recombinant human BMP4. M3 medium consists of HCM SingleQuot Kit™ supplemented with 50 ng/ml human recombinant HGF and 20 ng/ml Oncostatin M. M4 medium is a medium containing Cellartis (registered trademark) Hepatocyte Maintenance Medium. Both mediums of the upper layer and lower layer were exchanged with fresh mediums and growth factor every two days.

(4) Immunocytochemistry

Cells were fixed in PBS containing 4% paraformaldehyde, permeabilized with 0.1% Triton X-100 and blocked with PBST (0.1% Tween-20 in PBS) containing 20% Blocking One (Nacalai Tesque, Japan). Antibodies were diluted with PBST (0.1% Tween-20 in PBS) containing 20% Blocking One (Nacalai Tesque, Japan). The cells were counterstained with 6-diamidino-2-phenylindole (DAPI).

The antibodies used were as follows: rabbit anti-AFP antibody (Dako, Glostrup, Denmark), goat anti-ALB antibody (Bethyl), mouse anti-Oct3/4 antibody (Santa Cruz), rabbit anti-Oct3/4 antibody (Cell Signaling), goat anti-Sox17 antibody (R&D Systems) and Alexa 568-conjugated and Alexa 488-conjugated antibodies (Invitrogen). Positive cells versus total cells (DAPI-positive cells) were determined by using the ImageXpress Micro cellular imaging system (Molecular Devices).

(5) RT-PCR Analysis

RNA was extracted from iPS cells by using the RNeasy micro-kit or Qiaxol (Qiagen, Germany) and then treated with DNase (Qiagen). For reverse transcription reaction, 2.5 μg RNA was subjected to reverse transcription using PrimeScript™ RT Master Mix. For real-time PCR analysis, the mRNA expression was quantified with SyberGreen on a StepOne Plus (Applied Biosystems, Foster City, Calif.). The PCR conditions were as follows: a cycle consisting of initial denaturation at 95° C. for 30 sec., denaturation at 95° C. for 5 sec., and annealing/extension at 60° C. for 30 sec., was repeated 40 times. Target mRNA level was expressed as an arbitrary unit and determined using the ΔΔ CT method. PrimerArray Hepatic Differentiation (Human) (TaKaRa PH017) containing primer pairs, which were optimized for real-time RT-PCR analysis for 88 genes associated with hepatic differentiation and 8 housekeeping genes, was used. Details of the primers are listed in FIGS. 7 and 8.

(6) Human Primary Hepatocytes

Commercially available cryopreserved primary hepatocytes (PH) were used (Bioreclamation IVT, Cat. No. M00995-P, Lot no. FOS, >$5.0\times10^6$ cells/vial). For real time PCR analysis using PrimerArray Hepatic Differentiation, RNA was extracted from cryopreserved primary hepatocytes without subjecting to pre-culture. For CYP activity, cryopreserved primary hepatocytes were thawed, resuspended at a concentration of $7.0\times10^5$ living cells/mL in InVitroGRO™ CP Medium mixed with Torpedo™ Antibiotic Mix, in accordance with the manufacturer's instruction (BioreclamationIVT) and seeded onto BioCoat™ collagen I 24-well microplates (Corning) so as to obtain a density of $3.5\times10^5$ cells/well. The medium was exchanged with William's E medium containing CM4000 (without phenol red; Life technologies), after 4 to 6 hours (h) and on the following day. CYP activity assay was started 4 hours (pre-4 h) or 48 hours (pre-48 h) after seeding.

(7) CYP Activity Assay

CYP 1A2, 2C9, 2C19, 2D6 and 3A4 activities in human iPS cell-derived hepatocytes were evaluated on day 32 and day 47 of initiation of differentiation. PHs pre-cultured for 4 h or 48 h were used as references. The cultures of human iPS cell-derived hepatocytes or PHs were washed with warm Willim's E medium supplemented with PS. Assay was started by adding a medium containing a cocktail (mixture) of the following chemicals: 50 μM phenacetin, 10 μM bufuralol hydrochloride (Sumika Chemical Analysis Service, Ltd.), 5 μM diclofenac, 100 μM S-mephenytoin (Sumika Chemical Analysis Service, Ltd.), 5 μM midazolam and 50 μM Testosterone. Volumes of the medium added were 500 μl to the PH; 300 μl to the upper chamber and 600 μl to the lower chamber of the transwell CV membrane. After 1, 2, 6 and 24 hrs., 100 μl and 300 μl of supernatants were collected from the upper and lower chambers, respectively, and cryopreserved at −80° C. The supernatant was thawed and metabolites, i.e., acetaminophen, 1'-OH bufuralol, 4'-OH dicrofenac, 4-OH-mephenytoin, 1-OH midazolam and 6b-OH testosterone, were subjected to LC/MS analysis. For human iPS cell-derived hepatocytes, chemicals were added to both the upper and lower chambers and supernatants were collected from both chambers and combined. The mass of proteins per well was quantified by using the Pierce BCA protein assay kit (ThrmoFisher, Rockford, Ill.) in accordance with the manufacturer's instructions. Metabolite concentrations were normalized by the protein mass.

(8) Statistics

Data were expressed by the mean±S.D. (n=3). Differences between groups were analyzed by Student's t-test or one-way ANOVA using the post-hoc Dunnett's test. In legends of individual figures, the statistical analysis and P-value are separately shown. In the case of Student's t-test, *p<0.05 or **p<0.01 is considered as being significant; whereas in the case of one-way ANOVA using the post-hoc Dunnett's test, § P<0.05 or §§ P<0.01 is considered as being significant.

(9) Principal Component Analysis

The results are visualized. For mapping the expression profiles of 8 house-keeping genes and 88 hepatic differentiation genes in human iPS cell-derived hepatocytes differentiated on Collagen Vitrigel (CV), nanofiber (NF) or ordinary cell-culture plate (2D), principal component analysis (PCA) was performed by using a JMP software (SAS Institute Japan).

(B) Results (1) Hepatic Differentiation of Human iPS Cells on Collagen Vitrigel Membrane The present inventors previously disclosed that an NF matrix promotes in vitro hepatic differentiation of pluripotent stem cells. Here, to search other matrices that can potentiate hepatic differentiation, the present inventors checked the effect of Collagen Vitrigel (CV) membrane in potentiating the differentiation of human iPS cells into hepatocytes, in comparison with an NF matrix.

In this study, a human iPS cell line, i.e., ChiPS18 (Asplund et al., 2015, Stem Cell Rev. Reports), was used, which was reported to show a good differentiation efficiency into hepatocytes. The culture procedure for undifferentiated human iPS cells developed by the present inventors was optimized as described in the section "Materials and Methods". First, human iPS cell-derived endoderm cells were prepared by culturing ChiPS18 on M15 feeders for 3 days and collected on day 3 (D3) (FIG. 1A, B). The human iPS cell-derived endoderm cells were stocked as frozen cells. The human iPS cell-derived endoderm cells were confirmed, when thawed, to exhibit 92.8±0.14% SOX17 positive and 0.16±0.02% OCT3/4 positive, and then, cultured overnight (FIG. 1C).

To perform hepatic differentiation, the human iPS cell-derived endoderm cells were thawed, seeded onto a CV membrane, an NF matrix or an ordinary cell-culture 2D plate (2D) and cultured while continuously exchanging the medium to differentiate into the (destined) liver. More specifically, M2 medium was used for culturing from day 3 to 7 after initiation of differentiation, M3 medium from day 5 to 15 and then M4 medium from day 15 to 30 or 47. Immunocytochemical analysis of the human iPS cell-derived differentiated cells revealed that human iPS cell-derived cells were differentiated into α-fetoprotein-single positive (AFP+) hepatic progenitor cells (69.6%) and AFP/albumin (ALB)-double positive hepatoblasts (28.3%) on day 15. The expression of AFP decreased to 36.1% and the expression of ALB single positive cells increased to 23.7% on day 20. On day 25, the expression of ALB-single positive cells was 54.3% (FIG. 1D); whereas, the expression of AFP single positive cells was approximately 6.2%. The human iPS cell-derived cells cultured on CV membrane had polygonal shapes, which suggested that these cells are hepatocytes (FIG. 1E).

(2) Human iPS Cell-Derived Hepatocytes Cultured on Vitrigel Exhibited More Matured Expression Profile than Those Cultured on Nanofiber Matrix.

To clarify the characteristics of the human iPS cell-derived hepatocytes, the present inventors carried out real time RT-PCR, by which the expressions of hepatic molecular markers were checked by using a primer set consisting of 88 known genes involved in hepatic differentiation and 8 housekeeping genes (FIG. 2; the full list of markers shown in FIGS. 7 and 8). In the real time RT-PCR, human iPS cell-derived hepatocytes cultured on CV membrane were compared to those cultured on an NF matrix (which was previously reported to be a potent matrix for supporting hepatic differentiation). As a control, RNA directly extracted from primary hepatocytes (PH) cryopreserved without pre-incubation, was used. The expression of markers of immaturity, such as AFP or Apolipoprotein A-IV (APOA4), which almost disappeared in the primary hepatocytes (PH), were observed in human iPS cell-derived hepatocytes cultured on CV; however the expression levels thereof were extremely low compared to the levels of those cultured on NF or in the ordinary cell-culture 2D environment (2D). Transcription factors such as prospero homeobox 1 (PROX1), hematopoietically expressed homeobox (HHEX) or nuclear receptor subfamily 1H4 (NR1H4; encoding farnesoid X receptor; FXR), which are known to promote the expression of the maturation markers, were upregulated in iPS cell-derived hepatocytes cultured on CV, compared to those cultured on an NF matrix. Markers of maturity highly expressed in primary hepatocytes, such as SERPINA1 (encodes α 1-antitrypsin; AAT) or asialoglycoprotein receptor 1 (ASGR1) (Peters et al., 2016 Development 143, 1475-1481), were found to be highly expressed in human iPS cell-derived hepatocytes cultured on CV, compared to those cultured on an NF matrix or an ordinary cell-culture plate. The expression level of ALB was approximately ⅙-fold of that in PH; whereas, the expression level of ASGR1ALB was approximately ⅓-fold of that in PH. Taken together, these transcription profiles suggest that human iPS cell-derived hepatocytes cultured on CV are more matured than those cultured on an NF matrix.

A phase II metabolizing enzyme, such as UGT1A1 (UDP glucuronosyltransferase 1 alpha 1), excretion transporters such as ATP-binding cassette and sub-family C3 (ABCC3 or MRP3) and uptake transporters, such as solute carrier organic anion transporter1B1 (SLCO1B1 or OATP1B1) and SLC22A1 (or OCT1; organic cation transporter1), were expressed in human iPS cell-derived hepatocytes cultured on CV at higher levels than in those cultured on an NF matrix (FIG. 2). These transcription profiles suggest a possibility that a more matured feature of the human iPS cell-derived hepatocytes was obtained by culturing on a CV membrane.

Subsequently, the expression profiles of metabolic enzymes were analyzed. Metabolic enzymes, such as cytochrome P450 (CYP) 1A1, 1A2, 2D6, 3A4 and 3A7, were expressed at higher levels in human iPS cell-derived hepatocytes cultured on CV compared to those cultured on NF (FIG. 3). Other CYP enzymes, such as CYP2A6, 2C8, 2E1 and 7A1 (involved in cholesterol metabolism) showed analogous expression levels between human iPS cell-derived hepatocytes cultured on CV and NF. Whereas a fetal CYP enzyme, i.e., CYP3A7, was expressed at a high level in human iPS cell-derived hepatocytes cultured on CV. It is noteworthy that CYP1A1 expression is higher than in PH and that CYP3A4 is approximately 1/50-fold of that in PH. It is also noteworthy that substantial expression of most of the CYP enzymes was observed from D31 to D41, and that the function of the cells was maintained for 10 days or more.

Other hepatic markers, for example, keratin 18 (KRT18) and T-box 3 (TBX3), were expressed in earlier human iPS cell-derived cells but the expression levels thereof reduced as days went after initiation of differentiation increased (FIG. 4). Expression of transferrin (TF) or nuclear receptor 1I3 (NR1I3; or constitutive androstane nuclear receptor, CAR) was also detected. Other maturation markers of the liver, such as the urea cycle enzymes including ornithine carbamoyltransferase (OTC), argininosuccinate lyase (ASL) and arginase (ARG1), and an enzyme involved in tryptophan metabolism including tryptophan 2,3-dioxygenase (TDO2) were expressed. Uptake transporters, i.e., solute carrier family 10A1 (sodium/bile acid cotransporter family; SLC10A1 or NTCP), SLCO2B1 (OATP2B1) and excretion transporters such as ABCB4 (MDR3) and ABCG2 (BCRP) were expressed in human iPS cell-derived hepatocytes.

Most of the maturation markers of the hepatocytes are more up-regulated in human iPS cell-derived hepatocytes cultured on CV than those on an NF matrix. Importantly, most of the maturation markers were substantially expressed in human iPS cell-derived hepatocytes on day 47, which suggests that human iPS cell-derived hepatocytes are functional and can be maintained for 10 days or more.

(3) Principal Component Analysis of iPS-Derived Cells

To obtain insights into the expression profile of the human iPS cell-derived differentiated cells, Principal Component Analysis (PCA) of the PrimerArray gene expression was carried out. The following features were clarified by PCA having the highest variance: human iPS cell-derived differentiated cells cultured on an ordinary 2D (plate), NF or CV on day 7, day 15 and day 27 or later, were classified into three different clusters. Of the clusters, human iPS cells on day 27 or later were mapped away from human iPS cells cultured on CV or 2D (FIG. 5A).

The genes that coordinate with the PC1 or PC2 axis are shown in FIG. 5B. For example, the genes that coordinate with the day-7 cell cluster are, e.g., FOXA2, TBX3, NODAL and LAMB1 genes, which are involved in endoderm differentiation. The genes that coordinate with the day-15 cell cluster are, e.g., AFP, KRT18, CYP7A1 and APOA4 genes, which are involved in early hepatic differentiation. Genes, such as SERPINA1, SLC22A1, NR1H4 and CYP1A2, which are involved in maturation of hepatocytes, coordinate with a cell cluster of day 27 or later.

The results suggest that the human iPS cell-derived hepatocytes cultured on CV membrane are analogous to matured hepatocytes and show a different gene expression profile from that cultured on NF or in the 2D environment.

(4) Functional Analysis of the Activity of Metabolic Enzymes in the Human iPS Cell-Derived Hepatocytes Since CYP1A2, CYP2C9, CYP2C19, CYP2D6 and CYP3A4 are cytochrome P450 enzymes mostly involved in drug metabolism in the liver, their enzymatic activities in the iPS cell-derived hepatocytes were examined. To evaluate the functions of the metabolic enzymes, a mixture of phenacetin, bufuralol hydrochloride, diclofenac, S-mephenytoin and midazolam was added, and respective metabolites, i.e., acetoaminophen, 1'-OH bufuralol, 4'-OH diclofenac, 4-OH mephenytoin and 1-OH midazolam were analyzed by LC/MS. In the series of experiments, primary hepatocytes pre-cultured for 4 hours (pre-4 h) and 48 hours (pre-48 h) were used as positive controls.

As results of actions of CYP1A2, 2C19, 2D6 and CYP3A4 in the human iPS cell-derived hepatocytes, metabolites were detected at high levels. The levels of the metabolites generated by CYP1A2 and CYP3A4 actions were approximately 0.2 and 0.5 nmol/mg protein/min in human iPS cell-derived hepatocytes on day 47, respectively, which were significantly higher than those in primary hepatocytes of pre-4 h and primary hepatocytes of pre-48 h. CYP2C19 activity on D32 was significantly higher than that of primary hepatocytes of pre-48 h; whereas, the activity of human iPS cell-derived hepatocytes on D47 was almost equivalent to that of primary hepatocytes of pre-4 h and higher than that of primary hepatocytes of pre-48 h. The CYP2D6 activity of human iPS cell-derived hepatocytes on D32 or D47 was almost equivalent to that of primary hepatocytes of pre-48 h. CYP2C9 activity was also lower than that in primary hepatocytes of pre-48 h; however, it was detected (FIG. 6).

Importantly, the results of the present invention also demonstrate that the activities of metabolizing enzymes, i.e., CYP1A2, CYP2C9, CYP2C19, CYP2D6 and CYP3A4, in human iPS cell-derived hepatocytes cultured on CV can be maintained for two weeks or more in culture.

(C) Discussion

In the current study, the present inventors demonstrated the generation of human iPS cell-derived hepatocytes that exhibit features of the mature hepatocytes, by culturing human iPS cell-derived endoderm cells on CV membranes. The human iPS cell-derived endoderm cells cultured on CV membrane gradually down-regulated the expression of immature markers of AFP or APOA4, then up-regulated mature hepatocyte transcription factors, such as PROX1, HHEX, and nuclear receptors such as NR1H4 and NR1I3. Up-regulation of nuclear receptors is important in that many target genes important for hepatic differentiation and maturation are regulated by nuclear receptors. NR1H4 is an important transcription factor that regulates bile acid synthesis, detoxification and transport, and is also involved in the transcriptional regulation of CYP3A4, CYP7A1, SLCO1B1 (Calkin and Tontonoz, 2012, Nat Rev Mol Cell Biol 13, 213-224). NR1I3 is known to influence the expression of a broad spectrum of metabolizing phase I CYP enzymes, and enzymes involved in phase II drug metabolism, as well as the transporter proteins (Godoy et al., 2013, cells signaling and ADME). These features led to upregulation of a mature hepatocyte markers ALB, ASGR1 and SERPINA1 at later stages of human iPS cell differentiation. Drug uptake transporters SLCO1B1, SLC22A1, phase II enzymes UGT1A1, excretion transporter ABCC3 and many CYP enzymes are expressed in the human iPS cell-derived hepatocytes. CYP enzymes such as CYP1A1, 1A2, 2A6, 2C8, 2D6, 2E1 and 3A4 that are involved in the metabolism of a significant proportion of the drugs in the liver (Terada and Hira, 2015, J. Gastroenterol. 50, 508-519), are expressed at a substantial level in the human iPS cell-derived hepatocytes cultured on CV membrane. The human iPS cell-derived hepatocytes expressed CYP3A4 at about 1/50-fold of that of PH (no pre-culture). Particularly, it is important that the activities of metabolic enzymes, i.e., CYP1A2, 2D6, 2C9, 2C19 and 3A4, were observed. Of them, CYP1A2 and CYP3A4 activities, in human iPS cell-derived hepatocytes were higher than those in primary hepatocytes (pre-4 h); CYP2C19 activity was higher than primary hepatocytes (pre-48 h); and CYP2D6 activity was equivalent with that of primary hepatocytes (pre-48 h). Enzyme activities were observed from D32 up to D47 after initiation of culture in human iPS cell-derived hepatocytes, thereby suggesting that the metabolic enzyme activities were maintained for at least two weeks.

The present inventors previously reported the importance of basement membrane substratum in potentiation of differentiation of ES cells or iPS cells through activation of integrin beta 1. ES cells or iPS cells sense and transmit extracellular signals, and secrete heparin sulfate proteoglycan (HSPG), which acts in the vicinity of the cells with growth factor receptors to mediate inducing factor signals (Higuchi et al., 2010, J. Cell Sci.; Shiraki et al., 2011, PLoS One 6, 1-10). It was previously reported that dedifferentiation of hepatocytes and a reduction of liver functions in a 2D cell culture, and that cells in the liver are mechanosensitive, and the stiffness of the matrix is important (Godoy et al., 2009, Hepatology 49, 2031-2043; Wells, 2008, Hepatology 47, 1394-1400). Matrix that provides 3D microenvironment mimicking the extracellular matrices could support ESC/iPSC differentiation (Gieseck et al., 2014, PLoS One 9; Yamazoe et al., 2013, J. Cell Sci. 126, 5391-9). CV membrane was reported to support 3-D structure formation, and provide an appropriate stiffness, which might be an important key for its potentiation for maturation of the iPS cell-derived hepatocytes. The present inventors also observed enhanced cell adhesion of human iPS cell-derived endoderm cells on CV membrane, which led to an increased cell viability upon replating of the human iPS cell-derived endoderm cells. The permeability of the CV membrane might be also an important factor to facilitate the maturation of human iPS cell-derived hepatocytes. Taken together, CV membrane provides a suitable environment mimicking in-vivo and potentiated differentiation and maturation of the human iPS cell-derived hepatocytes.

Another point to be noted in our current protocol is the use of frozen iPS-derived endoderm cell lines. M15 was shown to derive endoderm cells from ESC/iPSC efficiently (Shiraki et al., 2008, Stem Cells 26, 874-85). By using the M15 system, a large number of human iPS cell-derived endoderm cells could be obtained efficiently, which allowed rapid differentiation of the human iPS cell-derived hepatocytes. Generally, $4\times10^7$ human iPS cell-derived endoderm cells could be obtained from one batch of M15 feeders on a 100 mm diameter plate, starting from $5\times10^5$ undifferentiated human iPS cells.

It is reported that hepatic differentiation potency differs among human ES cells and iPS cell lines (Kajiwara et al., 2012, Proc. Natl. Acad. Sci. U.S.A 109, 14716; Takayama et al., 2014, Biomaterials 34, 1781-1789). Therefore, it is important to choose a competent iPS cell line that can be differentiated into the mature hepatocytes. Here, the present inventors used ChiPS18 cell line that has been previously reportedly to differentiate into mature functional hepatocytes (Asplund et al., 2015, Stem Cell Rev. Reports). The present inventors are currently using other cell lines and testing if CV membrane is applicable to different human iPS cell lines.

In summary, the present inventors found that CV membrane is a suitable substrate that supports the differentiation and maturation of human iPS cells into hepatocytes. The human iPS cell-derived hepatocytes grown on CV membrane by the present inventors exhibit many analogous characteristics to primary hepatocytes. It is remarkable that human iPS cell-derived hepatocytes exhibited a high metabolic CYP enzyme activity comparable to that of primary hepatocytes (4 h or 48 h pre-culture). The human iPS cell-derived hepatocytes expressed many matured hepatocyte markers at high levels. Taken together, the results obtained by the present inventors suggest the human iPS cell-derived hepatocytes generated resemble that of the hepatocytes and provide an excellent model for in vitro liver toxicity studies as well as disease modeling.

The contents of all publications, patents and patent applications cited herein are incorporated in the specification as their entirety by reference.

INDUSTRIAL APPLICABILITY

The present invention relates to hepatocytes and thus available in industrial fields using hepatocytes.

The invention claimed is:

1. A method for preparing hepatocytes or cells that can be differentiated into hepatocytes from pluripotent stem cells, comprising the following steps (1) to (4):

(1) culturing the pluripotent stem cells in a medium containing an activator of an activin receptor-like kinase-4,7;

(2) culturing the cells obtained in the step (1) in a medium containing a bone morphogenetic factor and a fibroblast growth factor;

(3) culturing the cells obtained in the step (2) in a medium containing an activator of a hepatocyte growth factor receptor and an activator of an oncostatin M receptor; and (4) culturing the cells obtained in the step (3) to obtain hepatocytes or cells that can be differentiated into hepatocytes, wherein in at least one of the steps (2), (3) and (4), the cells are cultured on a high-density collagen gel membrane.

2. The method according to claim 1, wherein in all of the steps (2), (3) and (4), the cells are cultured on the high-density collagen gel membrane.

3. The method according to claim 1, wherein the activator of an activin receptor-like kinase-4,7 is activin A; the bone morphogenetic factor is BMP4; the fibroblast growth factor is FGF10; the activator of a hepatocyte growth factor receptor is HGF; and the activator of an oncostatin M receptor is oncostatin M.

4. The method according to claim 1, wherein the high-density collagen gel membrane is a gel in a stable state produced by rehydration after the vitrification of a traditional hydrogel.

5. The method according to claim 1, wherein the high-density collagen gel membrane comprises collagen fibers with a density of 21 to 45% (W/V).

6. The method according to claim 1, wherein the high-density collagen gel membrane is prepared by:

(a) a gelation step wherein collagen sol is gelatinized, (b) a vitrification step wherein the gelatinized collagen is dried, and (c) a rehydration step wherein the vitrified material is converted into a transparent gel membrane by supplying water.

* * * * *